(12) United States Patent
Hussam et al.

(10) Patent No.: US 10,607,725 B2
(45) Date of Patent: Mar. 31, 2020

(54) SURGICAL OPERATIVE NOTES

(71) Applicants: Ali Adel Hussam, Columbia, MO (US); Nathan Bleigh, Kansas City, MO (US)

(72) Inventors: Ali Adel Hussam, Columbia, MO (US); Nathan Bleigh, Kansas City, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 663 days.

(21) Appl. No.: 14/077,392

(22) Filed: Nov. 12, 2013

(65) Prior Publication Data
US 2014/0074511 A1 Mar. 13, 2014

Related U.S. Application Data

(63) Continuation-in-part of application No. 13/648,653, filed on Oct. 10, 2012.
(Continued)

(51) Int. Cl.
G09B 23/28 (2006.01)
G16H 10/60 (2018.01)
G16H 10/20 (2018.01)

(52) U.S. Cl.
CPC .............. G16H 10/60 (2018.01); G09B 23/28 (2013.01); G16H 10/20 (2018.01)

(58) Field of Classification Search
CPC .. G06F 19/327; G06F 19/3475; G06F 19/324; G06Q 50/24; G09B 21/006; G09B 23/28
(Continued)

(56) References Cited

U.S. PATENT DOCUMENTS 7,802,183 B1 9/2010 Essin
2001/0016821 A1* 8/2001 DeBusk ................. G06F 17/30
705/2
(Continued)

FOREIGN PATENT DOCUMENTS

JP 2004-145507 5/2004
JP 2004-283316 10/2004

OTHER PUBLICATIONS

International Search Report & Written Opinion of Application No. PCT/US2013/020284, dated Jun. 21, 2013, pp. 1-15.
(Continued)

Primary Examiner — James B Hull
(74) Attorney, Agent, or Firm — Fish & Richardson P.C.

(57) ABSTRACT

A computer-implemented method comprising: retrieving a surgical center template for a surgical procedure that is performed by a surgical center; retrieving medical records pertaining to the patient; automatically pre-populating a portion of the template based on contents of the retrieved medical data records; transmitting, to a device used by a physician, the pre-populated template for presentation to the physician; receiving data pertaining to the surgical procedure, wherein the received data comprises at least one of data entered into a predefined data field of the plurality of predefined data fields and data indicative of a selection of a selectable field in the plurality of selectable fields; populating one or more other portions of the template with the received data pertaining to the surgical procedure; and generating, based on the populated template, a surgical operative note for the surgical procedure.

17 Claims, 19 Drawing Sheets

Related U.S. Application Data

(60) Provisional application No. 61/583,069, filed on Jan. 4, 2012.
(58) Field of Classification Search
 USPC ......................................................... 434/262
 See application file for complete search history.

(56) References Cited

U.S. PATENT DOCUMENTS

| | | | |
|---|---|---|---|
| 2002/0082865 A1* | 6/2002 | Bianco | G06F 19/3481 |
| | | | 705/2 |
| 2004/0111296 A1* | 6/2004 | Rosenfeld | G06F 19/322 |
| | | | 705/2 |
| 2005/0154613 A1 | 7/2005 | Kade | |
| 2005/0228815 A1* | 10/2005 | Carus | G06F 19/3487 |
| 2007/0232868 A1* | 10/2007 | Reiner | G06F 19/321 |
| | | | 600/300 |
| 2008/0103833 A1* | 5/2008 | Miglietta | G06F 19/322 |
| | | | 705/3 |
| 2008/0300915 A1 | 12/2008 | Molmenti et al. | |
| 2009/0287068 A1 | 11/2009 | Li et al. | |
| 2009/0313043 A1 | 12/2009 | Schoenberg | |
| 2010/0081118 A1 | 4/2010 | Dixit | |
| 2011/0161105 A1* | 6/2011 | Hussam | G06Q 10/10 |
| | | | 705/2 |
| 2011/0191122 A1 | 8/2011 | Kharraz Tavakol et al. | |
| 2012/0035956 A1* | 2/2012 | Cane | G06F 19/322 |
| | | | 705/3 |
| 2012/0215559 A1* | 8/2012 | Flanagan | G06Q 10/10 |
| | | | 705/3 |
| 2013/0035961 A1* | 2/2013 | Yegnanarayanan | G06F 19/322 |
| | | | 705/3 |
| 2013/0191154 A1* | 7/2013 | William | G06F 19/3487 |
| | | | 705/3 |
| 2013/0236867 A1* | 9/2013 | Avni | G09B 19/003 |
| | | | 434/247 |
| 2014/0006943 A1* | 1/2014 | Robbins | G06F 19/327 |
| | | | 715/273 |
| 2014/0099616 A1 | 4/2014 | Hussam | |
| 2015/0012299 A1* | 1/2015 | Kohli | G06F 19/322 |
| | | | 705/3 |
| 2015/0254431 A1* | 9/2015 | Gaertner | G06F 19/363 |
| | | | 705/2 |
| 2016/0125169 A1* | 5/2016 | Finn | G06F 3/04842 |
| | | | 707/692 |

OTHER PUBLICATIONS

Office Action in corresponding U.S. Appl. No. 13/648,653, dated Jan. 17, 2014, pp. 1-12.
Response to Office Action dated Jan. 17, 2014 in corresponding U.S. Appl. No. 13/648,653, dated Mar. 26, 2014, pp. 1-14.
Office Action in corresponding U.S. Appl. No. 13/648,653, dated Jul. 17, 2014, pp. 1-14.

* cited by examiner

FIG. 5

SURGICAL OPERATIVE NOTES

CLAIM OF PRIORITY

This application is a continuation-in-part of and claims priority under 35 U.S.C. § 120 to U.S. patent application Ser. No. 13/648,653, filed Oct. 10, 2012, which in turn claims priority under 35 U.S.C. § 119(e) to provisional U.S. Patent Application No. 61/583,069, filed on Jan. 4, 2012, the entire contents of each of which are hereby incorporated by reference.

BACKGROUND

A medical note is a document that includes the written notes of a physician.

SUMMARY

In general, one innovative aspect of the subject matter described in this specification can be embodied in methods that include the actions of retrieving a surgical center template for a surgical procedure that is performed by a surgical center, wherein the surgical center template comprises one or more of (i) a plurality of predefined data fields for entry of medical data, and (ii) a plurality of selectable fields for selection of an attribute of a patient on whom the surgical procedure is performed or an attribute of the surgical procedure; retrieving medical records pertaining to the patient; automatically pre-populating a portion of the template based on contents of the retrieved medical data records; transmitting, to a device used by a physician, the pre-populated template for presentation to the physician; receiving, from the device used by the physician, data pertaining to the surgical procedure, wherein the received data comprises at least one of data entered into a predefined data field of the plurality of predefined data fields and data indicative of a selection of a selectable field in the plurality of selectable fields; populating one or more other portions of the template with the received data pertaining to the surgical procedure; and generating, based on the populated template, a surgical operative note for the surgical procedure, with the surgical operative note comprising a summary of the surgical procedure and one or more details of the surgical procedure.

Other embodiments of this aspect include corresponding computer systems, apparatus, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Implementations of the disclosure can include one or more of the following features. Generating the surgical operative note comprises: structuring the surgical operative note into a plurality of operative portions, each of the plurality of operative portions related to a stage of a plurality of stages of the surgical procedure. The plurality of operative portions comprise a consultation portion, a pre-operative portion, an intra-operative portion, a post-operative portion, and a discharge portion. The surgical center template comprises: pre-operative portion for entry of data pertaining to a time period prior to the surgical procedure; an intra-operative portion for entry of data pertaining to performance of the surgical procedure; a post-operative portion for entry of data pertaining to an outcome of the surgical procedure or data related to recovery from the surgical procedure; and a discharge portion for entry of data pertaining to discharge from the surgical center. The surgical center template comprises a visualization related to the surgical procedure, and the method further comprises: labeling one or more portions of the visualization based on the medical information included in the medical records pertaining to the patient. Receiving, from the device used by the physician, data pertaining to the surgical procedure comprises: receiving data indicative of an annotation of a portion of the visualization. Receiving, from the device used by the physician, data pertaining to the surgical procedure comprises: receiving data indicative of a barcode associated with an implantable device that is used in the surgical procedure; and the method further comprises: retrieving data associated with the barcode from a data repository; updating a portion of the surgical center template with the retrieved data that is associated with the bar code; and transmitting, to the device used by the physician, the retrieved data for presentation with the surgical center template. The actions include determining, based on the received data pertaining to the surgical procedure, whether the surgical procedure is in compliance with national medical standards. The actions include determining that required data pertaining to the surgical procedure has not been received from the device used by the physician; and transmitting, to the device used by the physician for presentation to the physician, a notification that the required data has not been received.

All or part of the foregoing may be implemented as a computer program product including instructions that are stored on one or more machine-readable storage media (or hardware storage devices), and that are executable on one or more processing devices. All or part of the foregoing may be implemented as an apparatus, method, or electronic system that may include one or more processing devices and memory to store executable instructions to implement the stated functions.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE FIGURES

FIG. 5 shows an example of an operative note generated using a template.

Like reference symbols in the various drawings indicate like elements.

DETAILED DESCRIPTION

Described herein is a system for providing a physician of a surgical center with a template for generating an operative note for a surgical procedure that is performed by the surgical center. The template may include predefined data fields for entry of medical data and selectable fields for selection of an attribute of a patient on whom the surgical procedure is performed or an attribute of the surgical procedure. The template may be automatically pre-populated with contents of medical records pertaining to the patient before being presented to the physician. The physician may populate the template by entering data into a predefined data field or by selecting a selectable field. The operative note may be generated from the populated template and include a summary of the surgical procedure.

Figure 1A:
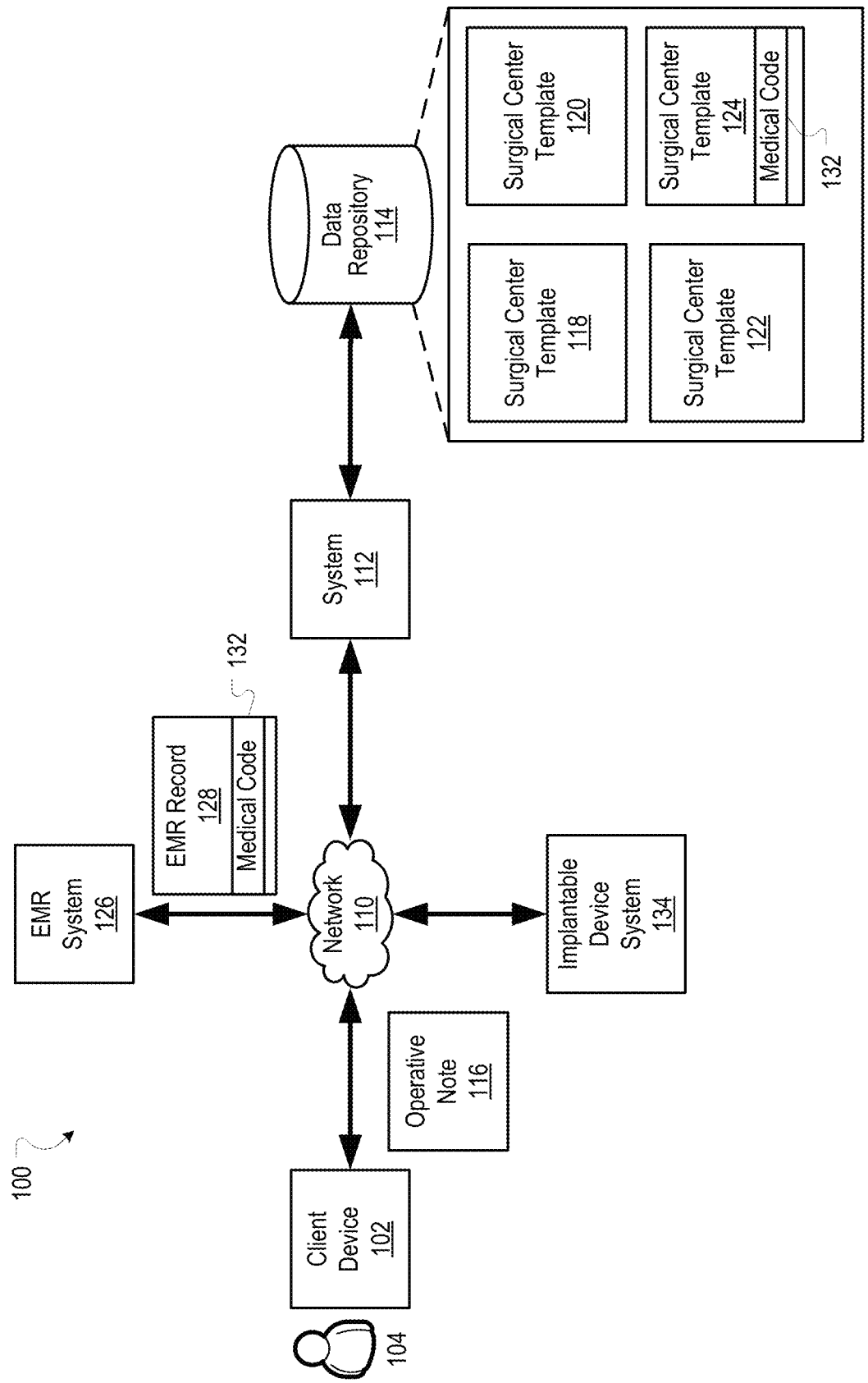
FIG. 1A is a conceptual diagram of a network environment for generating an operative note.

FIG. 1A is a conceptual diagram of a network environment 100 for generating an operative note 116 using a surgical center template, e.g., surgical center template 118, 120, 122, or 124. A surgical center template includes predefined data fields and selectable fields that are applicable to a surgical procedure. System 100 includes network 110, client device 102, electronic medical record (EMR) system 126, system 112, and data repository 114. In the example of FIG. 1A, system 112 is configured to generate the operative note 116.

In an example, client device 102 is used by user 104. User 104 may be a physician. User 104 may want to generate the operative note 116 about an upcoming surgical procedure, such as a knee surgery, to be performed on a patient. User 104 may send, to system 112, a request to generate the operative note 116. The request may include a patient identifier.

To generate the operative note 116, the system 112 is configured to identify which ones of surgical center templates 118, 120, 122, 124 are pertinent to the patient. There are various ways in which system 112 may determine which ones of surgical center templates 118, 120, 122, 124 are pertinent to the patient. In some examples, system 112 tracks upcoming appointments and/or procedures for the patient. System 112 may track the upcoming appointments, e.g., by retrieving data associated with the patient identifier from an external appointment booking system. When system 112 identifies an appointment of the patient, system 112 may use the appointment information to identify which ones of surgical center templates 118, 120, 122, 124 are applicable to the surgical procedure to be performed on the patient.

In another example, system 112 may use EMR record 128 associated with the patient identifier in identifying which ones of surgical center templates 118, 120, 122, 124 to use to generate the operative note 116. In this example, EMR system 126 is configured to store EMR records for various users. Generally, an EMR record includes an electronic version of a patient's medical record. In this example, EMR record 128 may include various medical codes, including, e.g., medical code 132. Generally, a medical code includes information uniquely identifying a particular type of diagnosis, medical condition, medical procedure, and so forth. There are various types of medical codes, including, e.g., diagnosis code, International Statistical Classification of Diseases and Related Health Problems ("ICD") codes (e.g., ICD-9 and ICD-10 codes), Current Procedural Terminology ("CPT") codes and other various diagnosis information and treatment information.

In the example of FIG. 1A, one or more of surgical center templates 118, 120, 122, 124 are associated with medical codes. For example, surgical center template 124 is associated with medical code 132. System 112 uses the medical codes included in EMR record 128 and the medical codes associated with one or more of the surgical center templates 118, 120, 122, 124 to identify which surgical center template is applicable to the surgical procedure that is to be performed on the patient. The system 112 may identify the surgical center template based on matches and/or similarities among medical codes in EMR record 128 and medical codes associated with the surgical center templates 118, 120, 122, 124. The system 112 searches data repository 114 for surgical center templates with a medical code that matches medical code 132. In the example of FIG. 1A, the system 112 identifies that surgical center template 124 is associated with medical code 132 that matches the medical code 132 included in the EMR record 128.

In the example of FIG. 1A, upon identifying the surgical center template 124 as applicable to the surgical procedure to be performed on the patient, the system 112 retrieves the surgical center template 124 and pre-populates a portion of the template 124 based on contents of the EMR record 128. For example, the system 112 may pre-populate a predefined data field of the template 124 with medical data from the EMR record 128, or pre-select a selectable field of the template 124 to indicate an attribute of the patient as indicated by contents in the EMR record 128.

In some examples, a surgical center template includes a visualization related to a surgical procedure or a portion of a body on which the surgical procedure is being performed. In this example, the system 112 may pre-label portions of the visualization included in the template based on medical information included in an EMR record pertaining to a patient. For example, for a patient who has a degenerative portion of a knee, the visualization shows a degenerative portion of a knee. Portions of the visualization of the degenerative portion of the knee may be pre-labeled to denote where the patient is experiencing certain symptoms, e.g., pain, degeneration, and prior surgical procedures.

The system 112 sends the pre-populated template 124 to the client device 102 for presentation to the user 104. After being presented with the pre-populated template 124, the user 104 may send, to system 112, data pertaining to the surgical procedure to be performed on the patient. The user 104 may enter the data into a predefined data field of the template 124, or the data may indicate a selection of a selectable field of the template 124.

In some examples, the user 104 may enter data by speaking into a microphone included or connected with the client device 102. In this example, the system 112 includes a speech recognition module to translate the words spoken by the user 104 into text for populating a data field of the template 124.

In some examples, the user 104 may scan a barcode attached to a patient implantable device using a barcode device reader included or connected with the client device 102. The system 112 may access an implantable device system 134 that is configured to store information for various patient implantable devices to retrieve data pertaining to the patient implantable device associated with the scanned barcode.

In some examples, the user 104 may enter data into the template 124 by hand drawing notations on a portion of a visualization included in the template 124. For example, the user 104 may hand draw a circle around a portion of the visualization to indicate a portion of the patient's body on which the surgical procedure is to be performed.

In response to receiving the data entered by the user 104, the system 112 populates the corresponding portions of the template 124 with the received data. When the user 104 has finished entering data using the template 124, the user 104 sends to the system 112 an indication that the user 104 has finished entering medical data. Upon receiving the indication, the system 112 may determine whether all portions of the template 124 have been completed. The system 112 may notify the user 104 when the system 112 determines that the user 104 has failed to complete a portion of the template 124.

Based on the medical data entered by the user 104, the system 112 may track compliance with medical standards, federal practices, or both. For example, the system 112 may determine whether a surgical procedure that is to be performed or has been performed on a section of anatomy, as described by the medical data entered by the user 104, is in compliance with national medical standards or practices. For example, system 112 retrieves from external data sources medical standard information, e.g., that specifies how a medical procedure is performed. System 112 then compares the entered medical data to the medical standard information, e.g., to make a compliance determination.

The system 112 may automatically send the medical data entered by the user 104 to the EMR system 126 to be included in the EMR record 128. Based on the populated template 124, the system 112 generates a surgical operative note 116 for the surgical procedure performed on the patient. The surgical operative note 116 may include a summary and one or more details of the surgical procedure. The system 112 may send the surgical operative note 116 to the client device 102 for presentation to the user 104. The system 112 may automatically send the surgical operative note 116 to a designated recipient, e.g., a medical billing system (not shown).

Figure 1B:
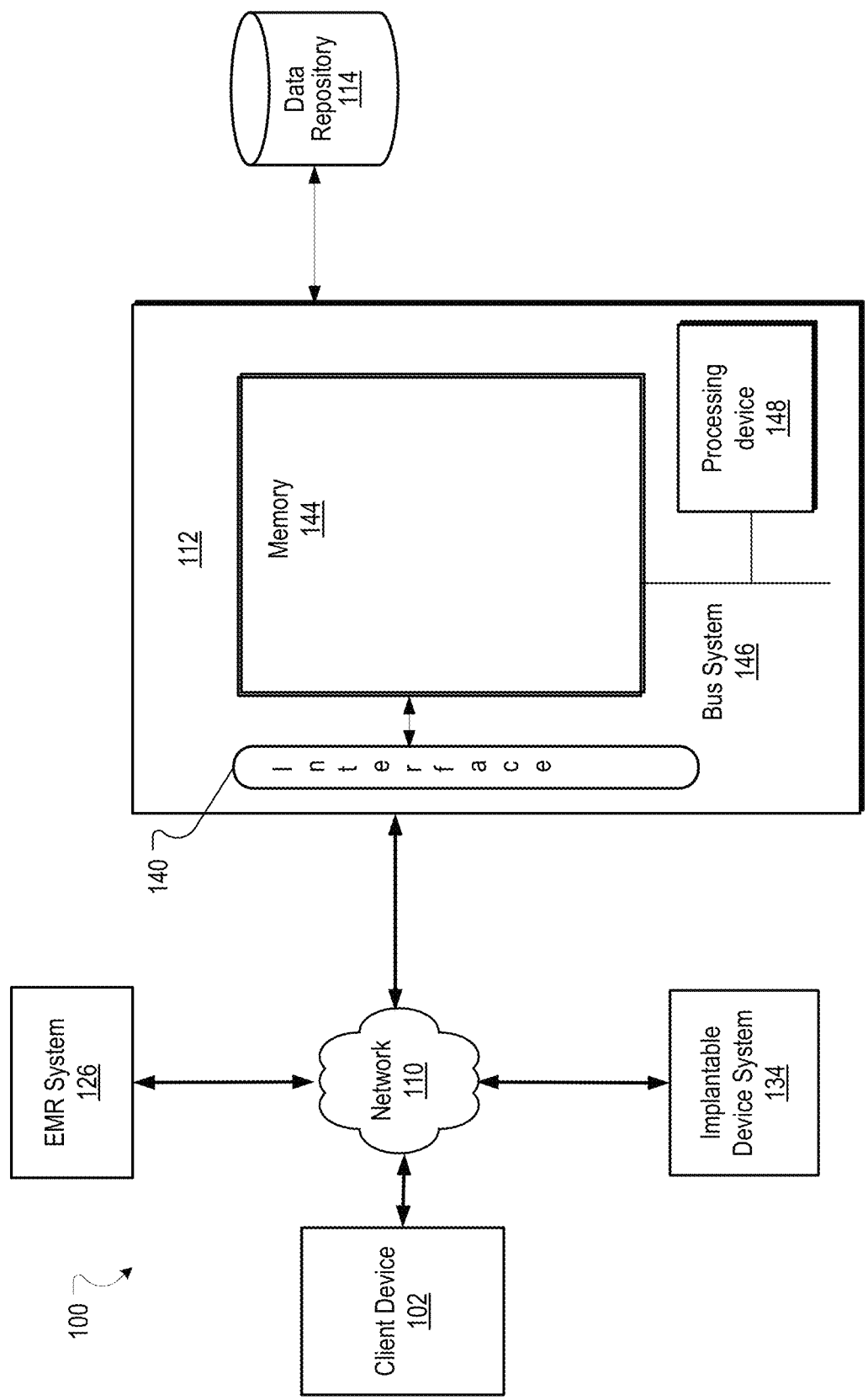
FIG. 1B is a block diagram of components of the network environment for generating an operative note.

FIG. 1B is a block diagram of components of the network environment 100 for generating operative notes. In FIG. 1B, client device 102 can be any sort of computing device capable of taking input from a user and communicating over network 110 with system 112, other client devices, and/or other systems. For example, client device 102 can be a mobile device, a desktop computer, a laptop, a cell phone, a personal digital assistant (PDA), a server, an embedding computing system, and so forth.

System 112 can be any of a variety of computing devices capable of receiving data, such as a server, a distributed computing system, a desktop computer, a laptop, a cell phone, a rack-mounted server, and so forth. System 112 may be a single server or a group of servers that are at the same location or at different locations.

The illustrated system 112 can receive data from the client device 102, EMR system 126, and implantable device system 134 via input/output (I/O) interface 140. I/O interface 140 can be any type of interface capable of receiving data over a network, such as an Ethernet interface, a wireless networking interface, a fiber-optic networking interface, a modem, and so forth. System 112 also includes a processing device 148 and memory 144. A bus system 146, including, for example, a data bus and a motherboard, can be used to establish and to control data communication between the components of system 112.

The illustrated processing device 148 may include one or more microprocessors. Generally, processing device 148 may include any appropriate processor and/or logic that is capable of receiving and storing data, and of communicating over a network (not shown). Memory 144 can include a hard drive and a random access memory storage device, such as a dynamic random access memory, or other types of non-transitory machine-readable storage devices. Memory 144 stores computer programs (not shown) that are executable by processing device 148 to perform the techniques described herein.

Figure 2A:
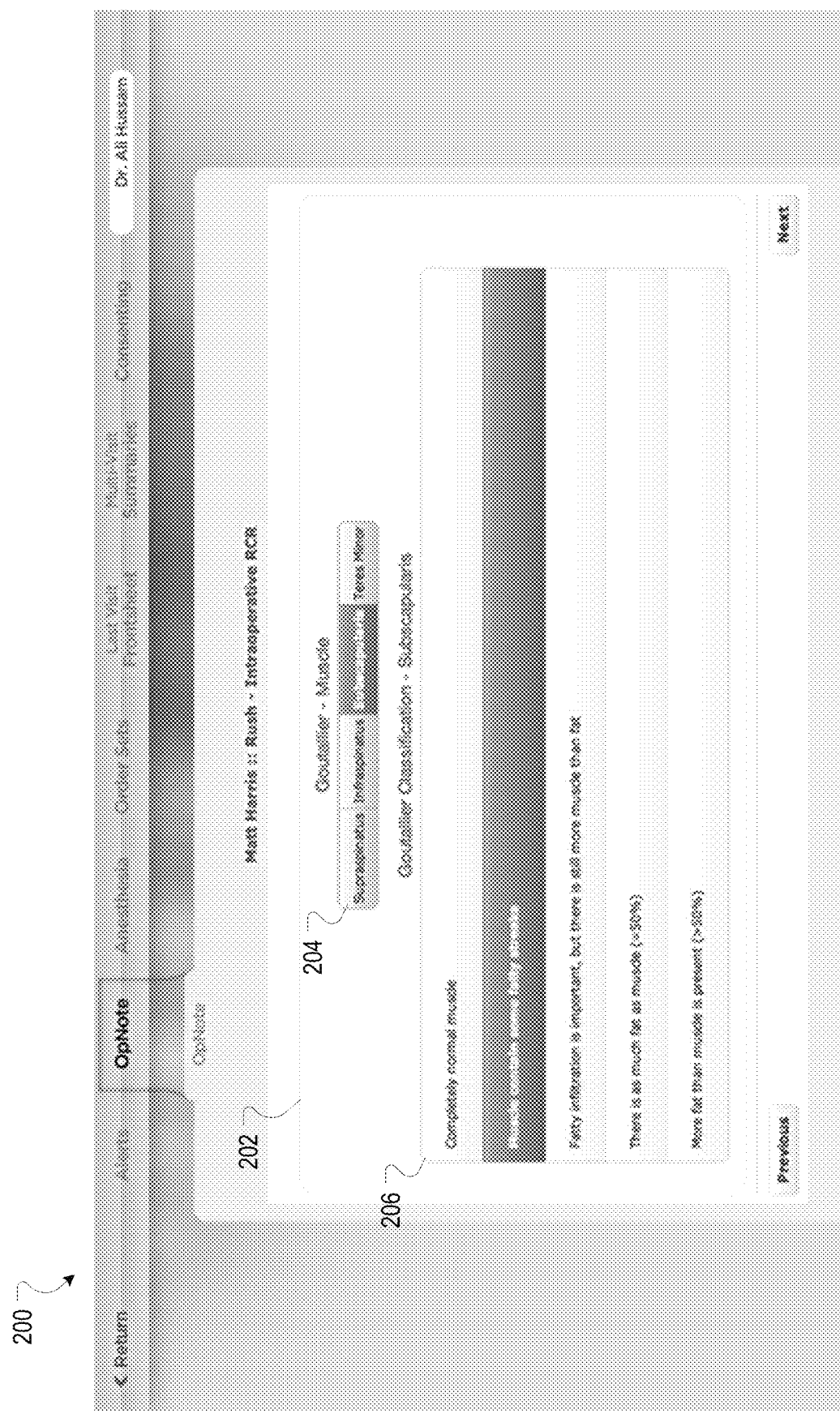
FIGS. 2A-4J show examples of graphical user interfaces that present portions of templates for generating operative notes.

FIGS. 2A-4J show examples of graphical user interfaces that present portions of templates for generating operative notes. Referring to FIG. 2A, system 112 generates a graphical user interface 200 that presents a portion 202 of a template pertaining to a rotator cuff repair (RCR) procedure performed on a patient. The portion 202 includes groups of selectable fields, e.g., groups 204 and 206. One or more of the selected fields in groups 204 and 206 may be pre-selected by the system 112 before presentation to the user based on contents of an EMR record associated with the patient, or selected by the user to enter medical data pertaining to a RCR performed on the patient. The selectable fields in group 204 are labeled with rotator cuff muscles. In the example of FIG. 2A, the selectable field in group 204 labeled with the rotator cuff muscle "Subscapularis" is selected. The selectable fields in group 206 are labeled with classifications of fatty degeneration of the cuff muscle indicated by the selected field in group 204. In the example of FIG. 2A, the selectable field in group 206 labeled with the classification "Muscle contain some fatty streaks" is selected.

Figure 2B:
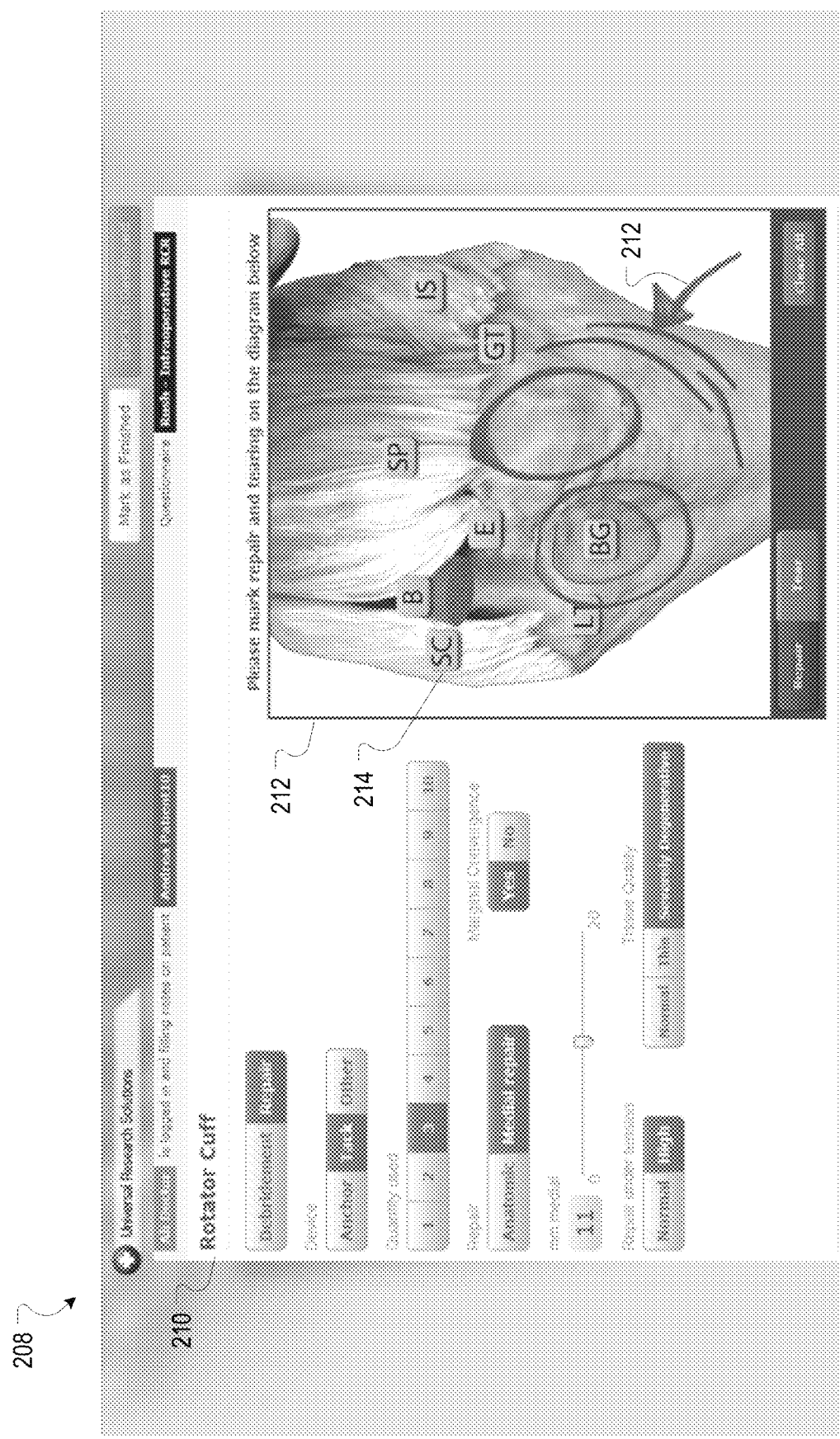

Referring to FIG. 2B, graphical user interface 208 presents a portion 210 of the template pertaining to the RCR procedure. The portion 210 includes visualization 212 showing a rotator cuff. The system 112 prepopulated the visualization 212 with labels, e.g., label 214, to include medical data contained in the patient's EMR record. The visualization 212 includes markings, e.g., marking 216, hand drawn by a user to enter medical data pertaining to the RCR procedure.

Figure 2C:
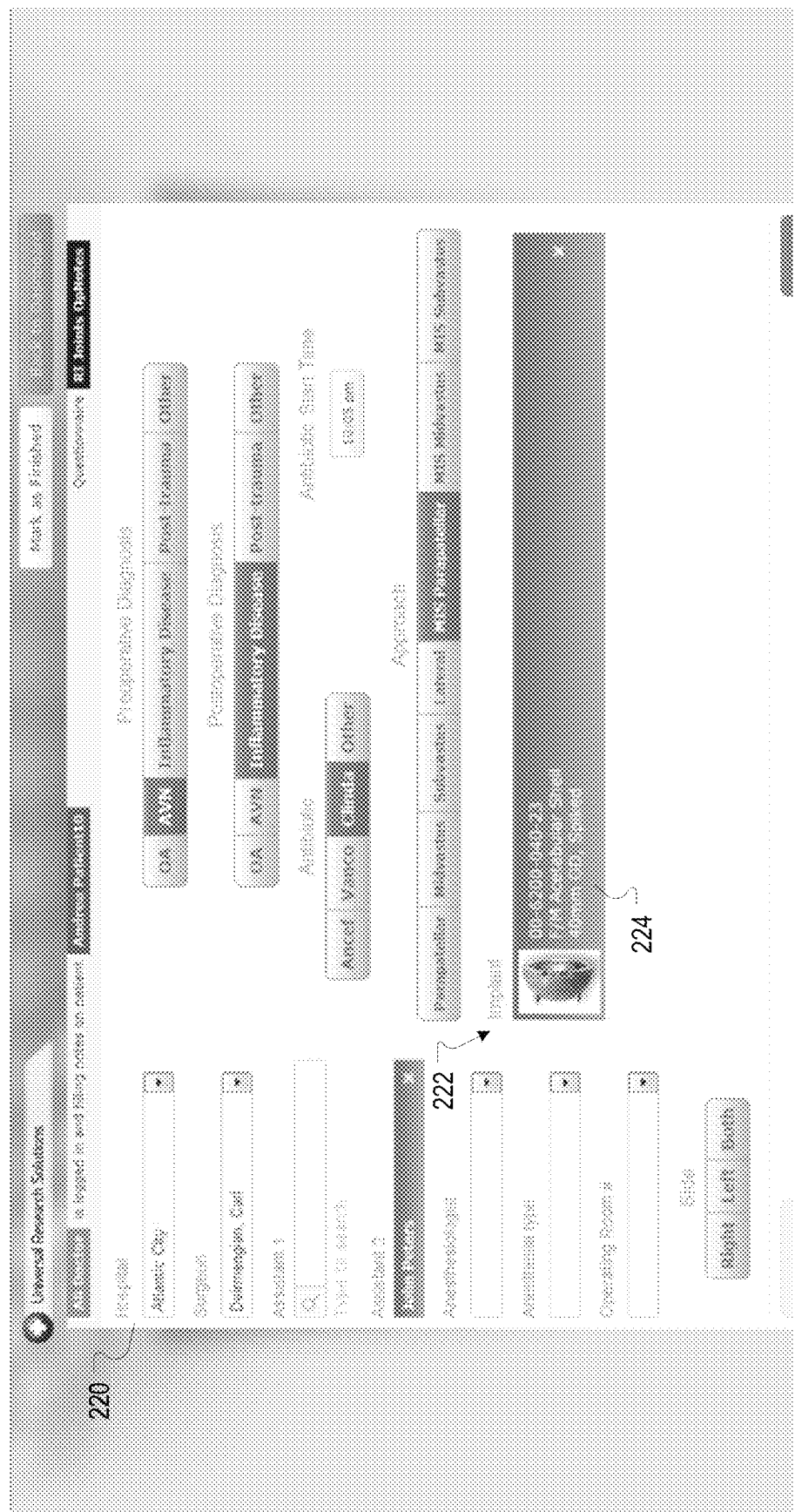

Referring to FIG. 2C, system 112 generates a graphical user interface 218 that presents a portion 220 of a template pertaining to a knee surgery. The system 212 prepopulates the implant section 222 of the portion 220 to include medical data 224 pertaining to a device implanted in the patient based on content included in the patient's EMR record.

Figure 3A:
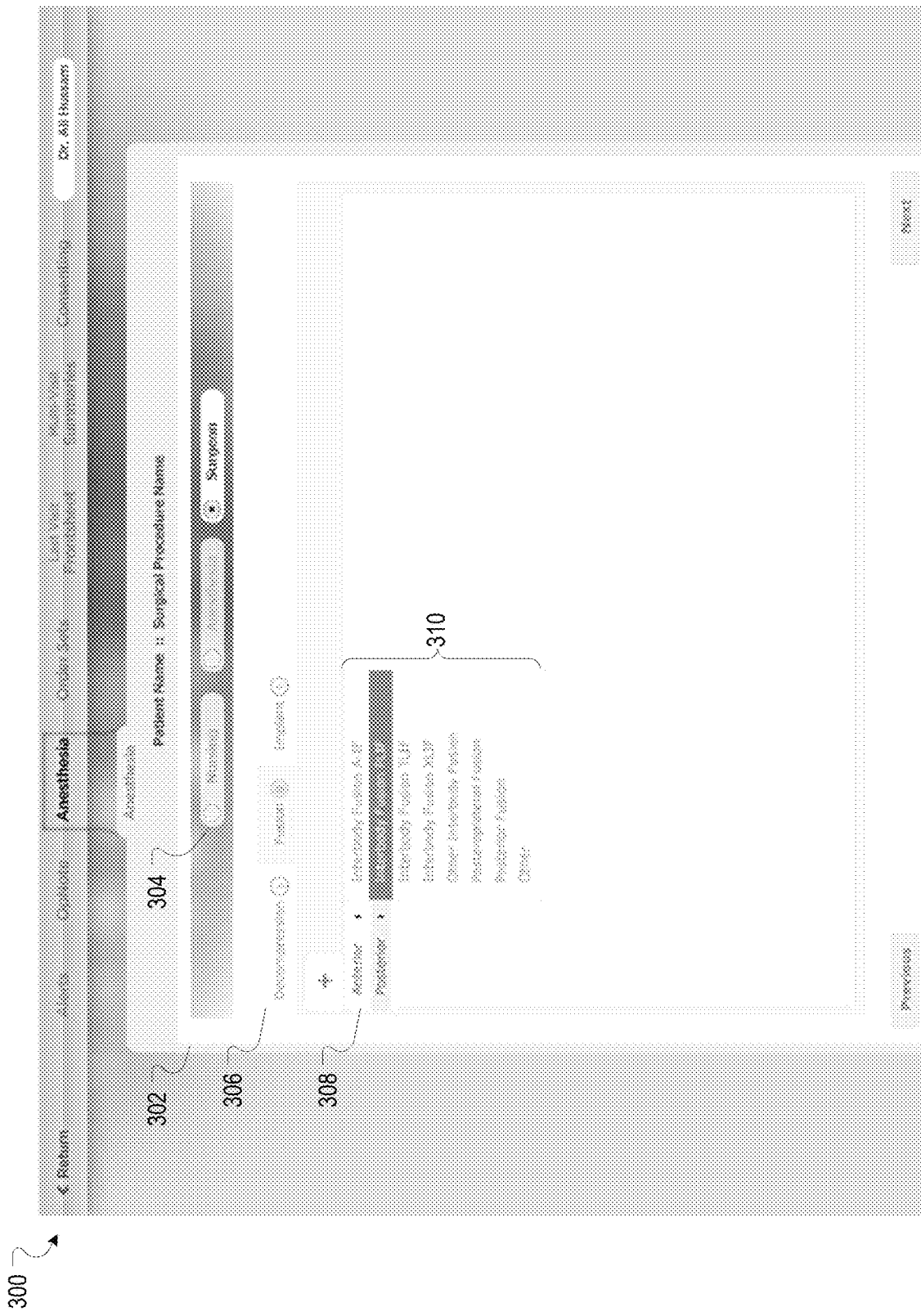

Referring to FIG. 3A, system 112 generates a graphical user interface 300 that presents a portion 302 of a template pertaining to spinal surgery performed on a patient. The portion 302 includes groups of selectable fields, e.g., groups 304, 306, 308, 310. One or more of the selected fields in groups 304, 306, 308, 310 may be pre-selected by the system 112 before presentation to the user based on contents of an EMR record associated with the patient, or selected by the user to enter medical data pertaining to a spinal surgery performed on the patient. The selectable fields in group 304 are labeled with titles of medical professionals involved in the spinal surgery or stages of the surgery. In FIG. 3A, the selectable field in group 304 labeled with the title "Surgeon" is selected. The selectable fields in group 306 are labeled with types of spinal surgery that can be performed on a patient. In FIG. 3A, the selectable field in group 306 labeled with "Fusion" is selected to indicate that a spinal fusion surgery is to be or was performed on a patient. The selectable fields in group 308 are labeled with a portion of a spine on which the spinal fusion surgery is performed. In FIG. 3A, the selectable field in group 308 labeled with "Posterior" is selected to indicate that the spinal fusion surgery is to be performed on a posterior portion of the patient's spine. The selectable fields in group 310 are labeled with types of spinal fusion surgery that can be performed on a posterior portion of a spine. In FIG. 3A, the selectable field in group 308 labeled with "Interbody Fusion PLIF" is selected.

Figure 3B:
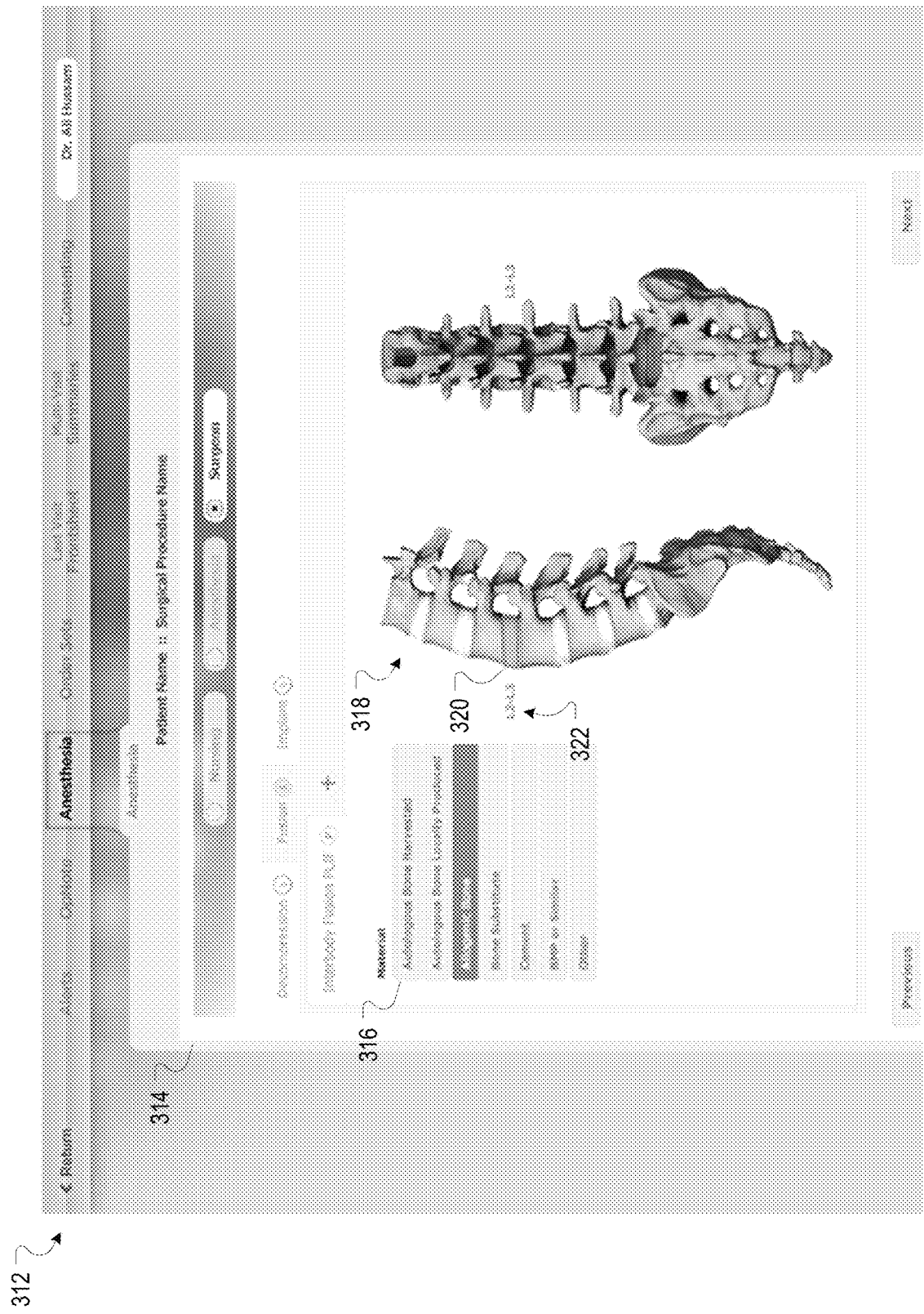

Referring to FIG. 3B, graphical user interface 312 that presents a portion 314 of the template pertaining to the spinal surgery may be displayed to the user, e.g., following the user selecting the selectable field in group 308 labeled with "Interbody Fusion PLIF". The portion 314 includes a group 316 of selectable fields. The selectable fields in group 316 are labeled with types of materials that can be used for the spinal surgery. In FIG. 3B, the selectable field in group 316 labeled with "Allogenic Bone" is selected. The portion 314 includes visualizations 318 showing different views of a portion of a spine on which the spinal surgery is performed. The visualizations 318 may include markings, e.g., marking 320, and labels, e.g., label 322, that indicate a portion of the spine on which the spinal surgery is performed. The visualizations 318 may be pre-annotated by the system 112 before presenting the portion 314 to the user based on contents of the EMR record associated with the patient, or marked-up and labeled by the user to enter medical data pertaining to the spinal surgery performed on the patient.

Figure 4A:
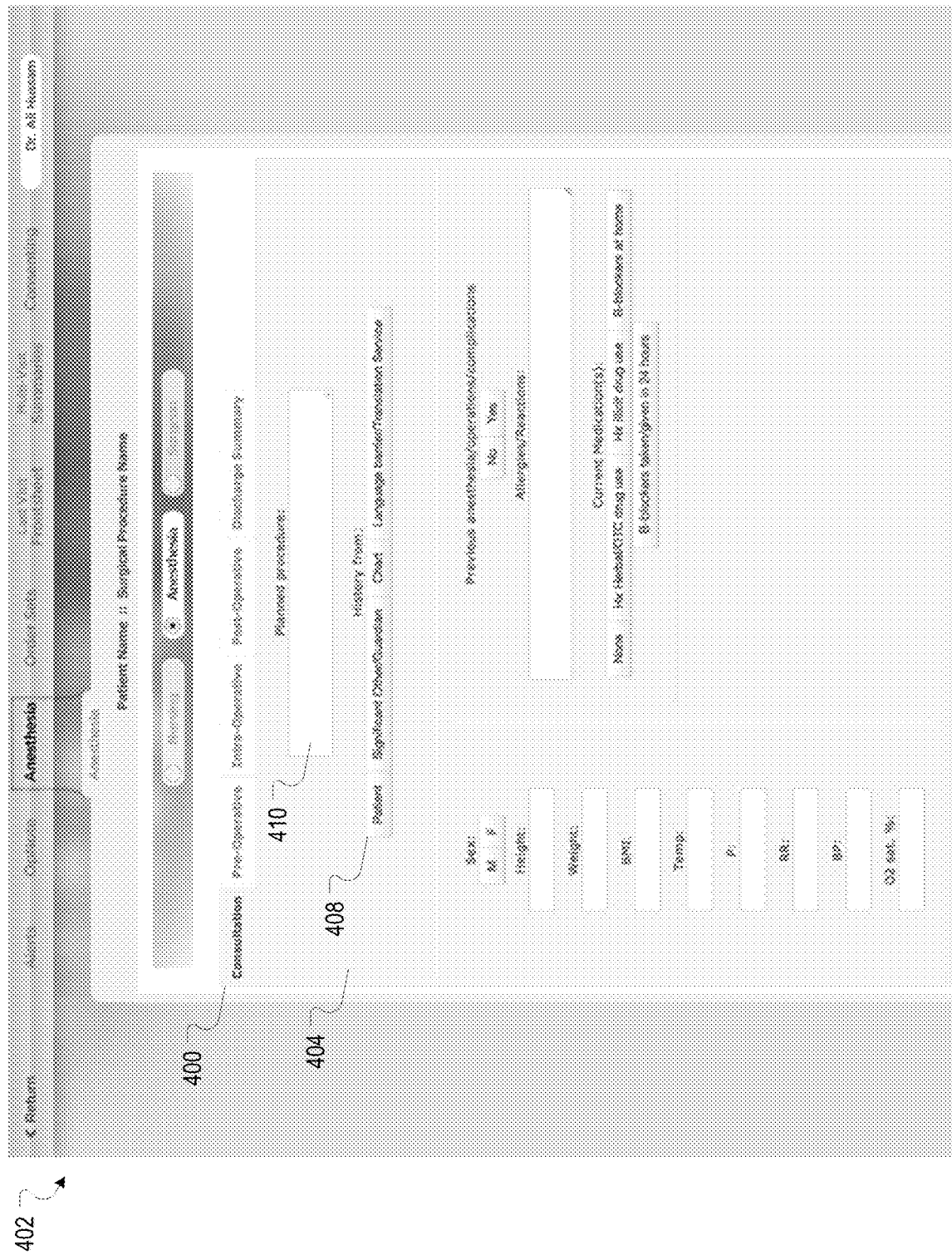
Figure 4B:
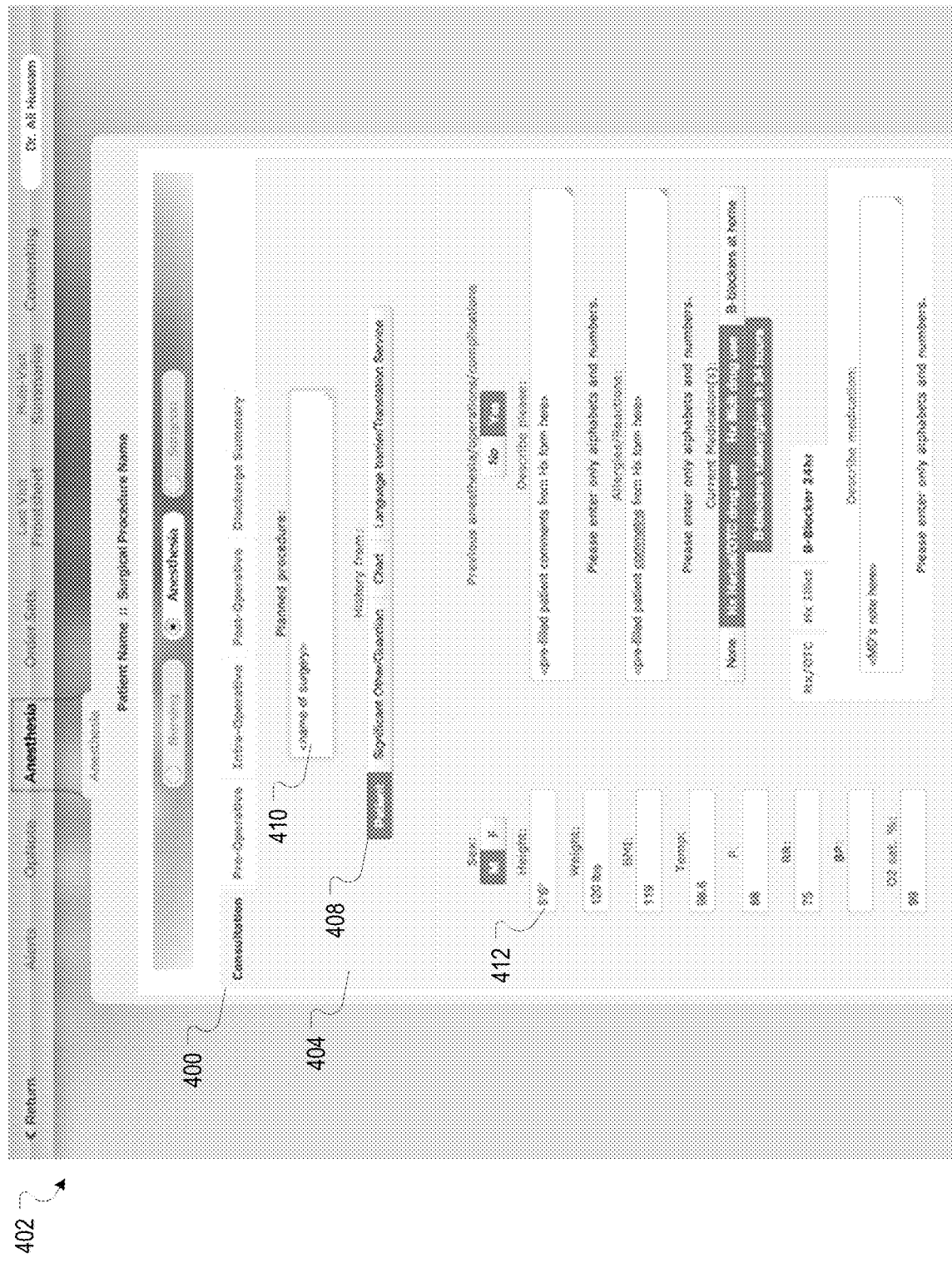
Figure 4C:
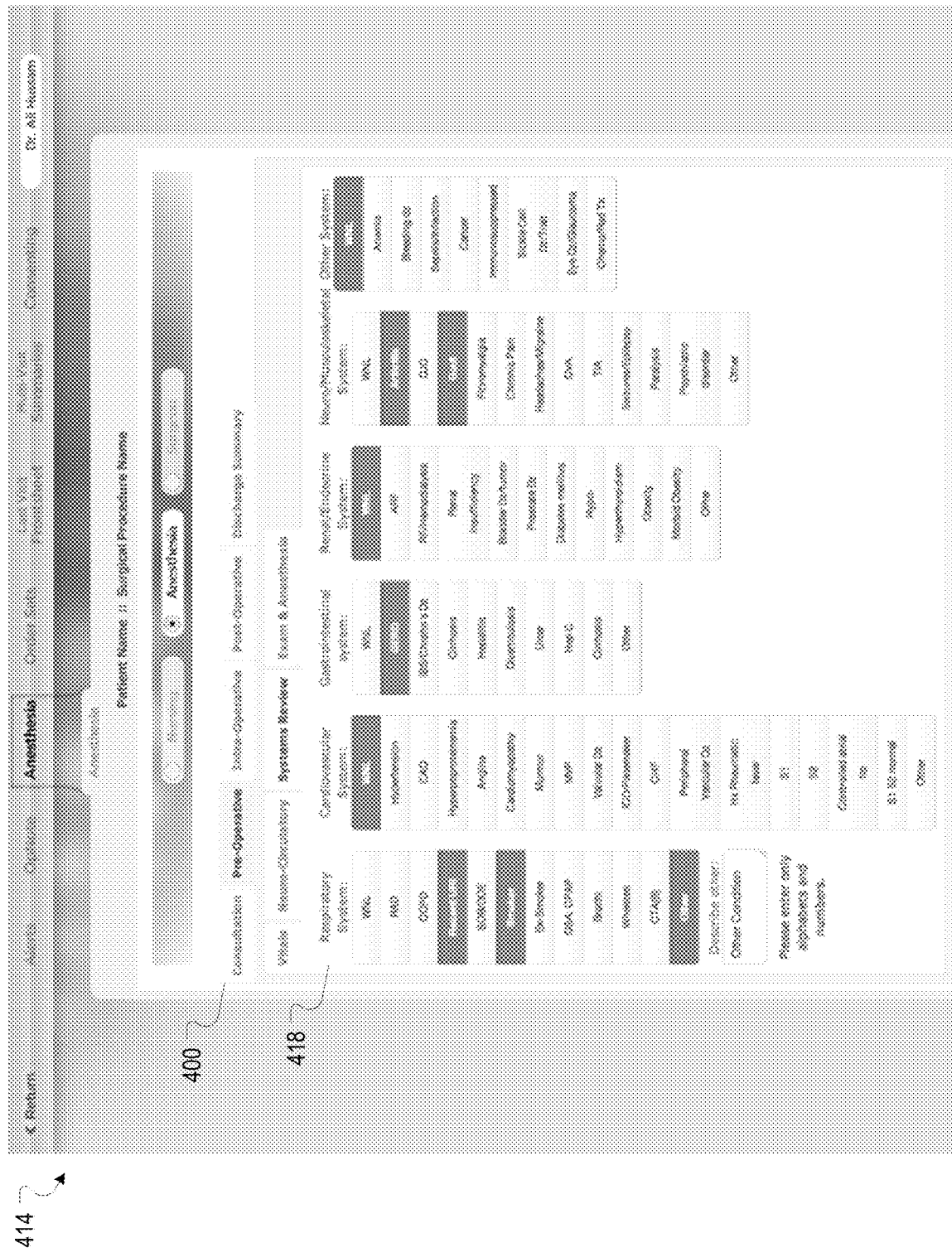
Figure 4D:
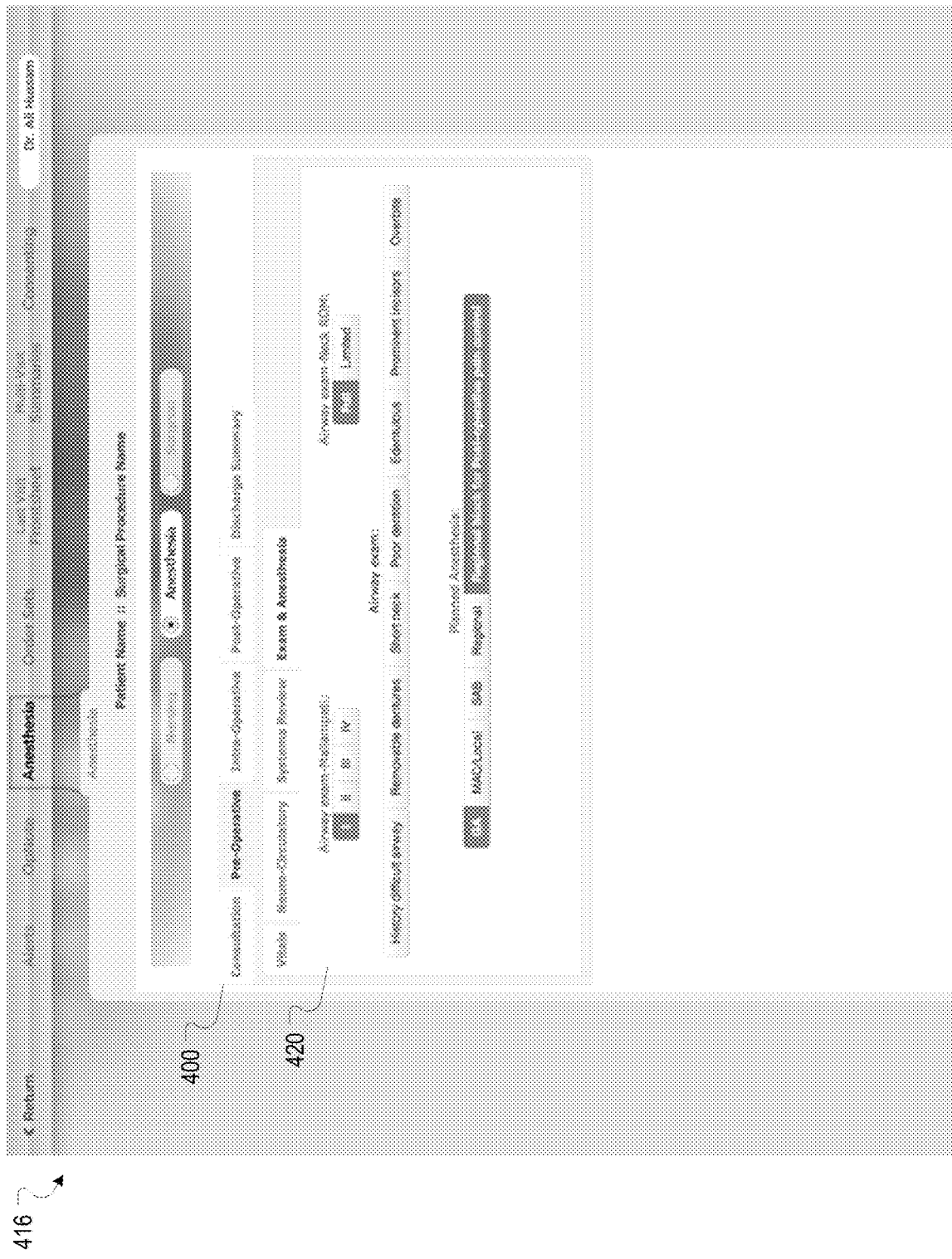
Figure 4E:
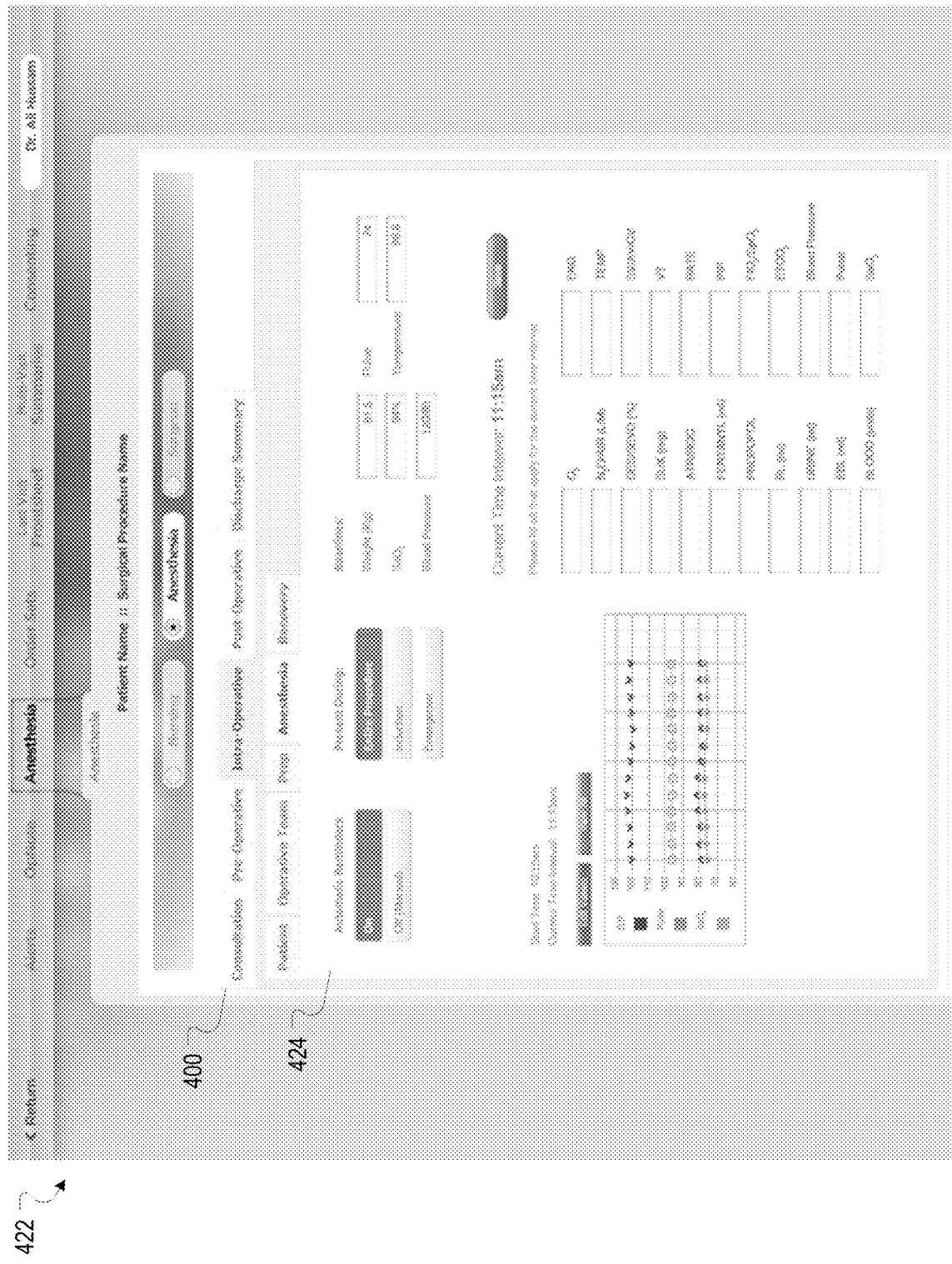
Figure 4F:
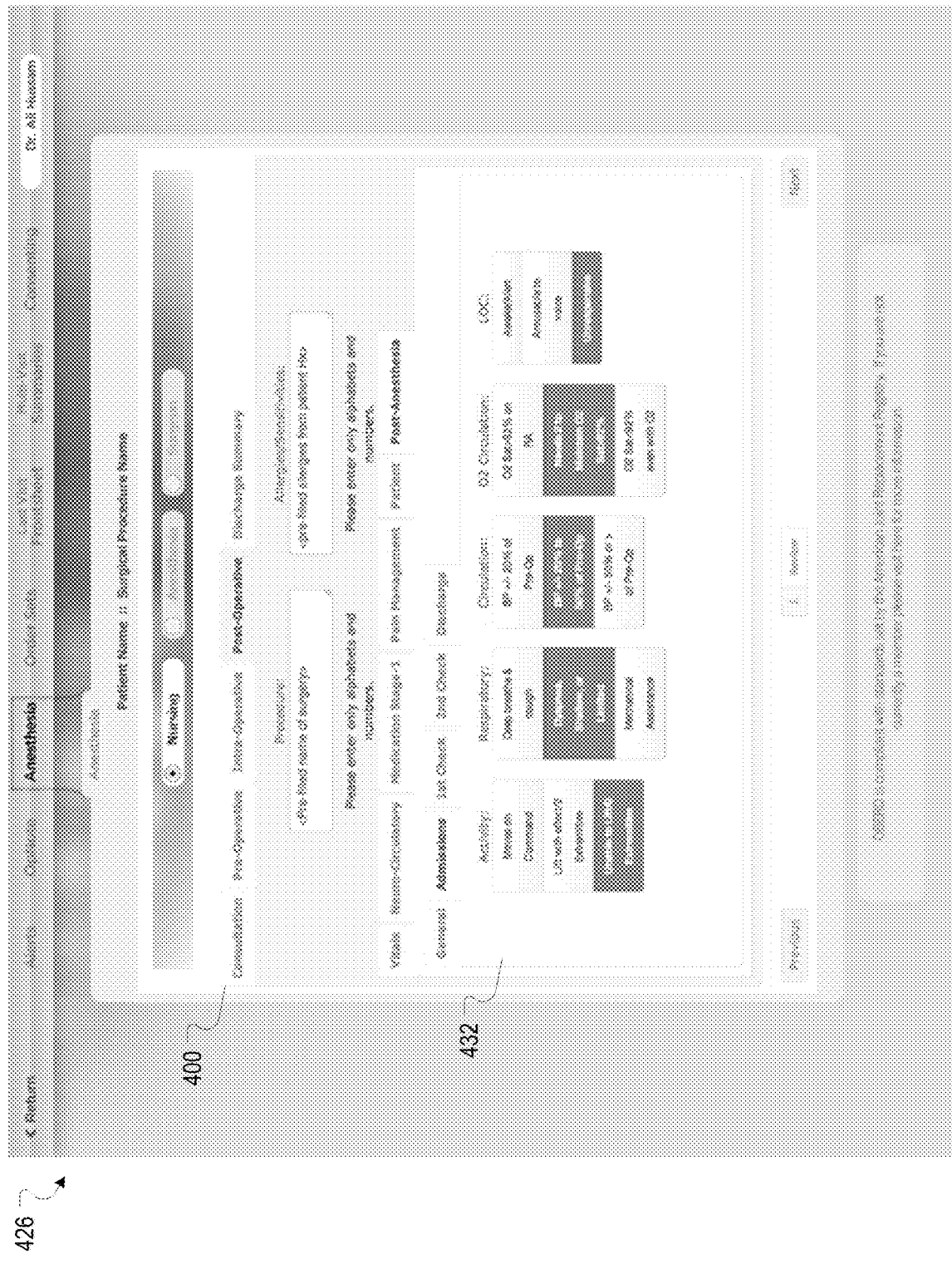
Figure 4G:
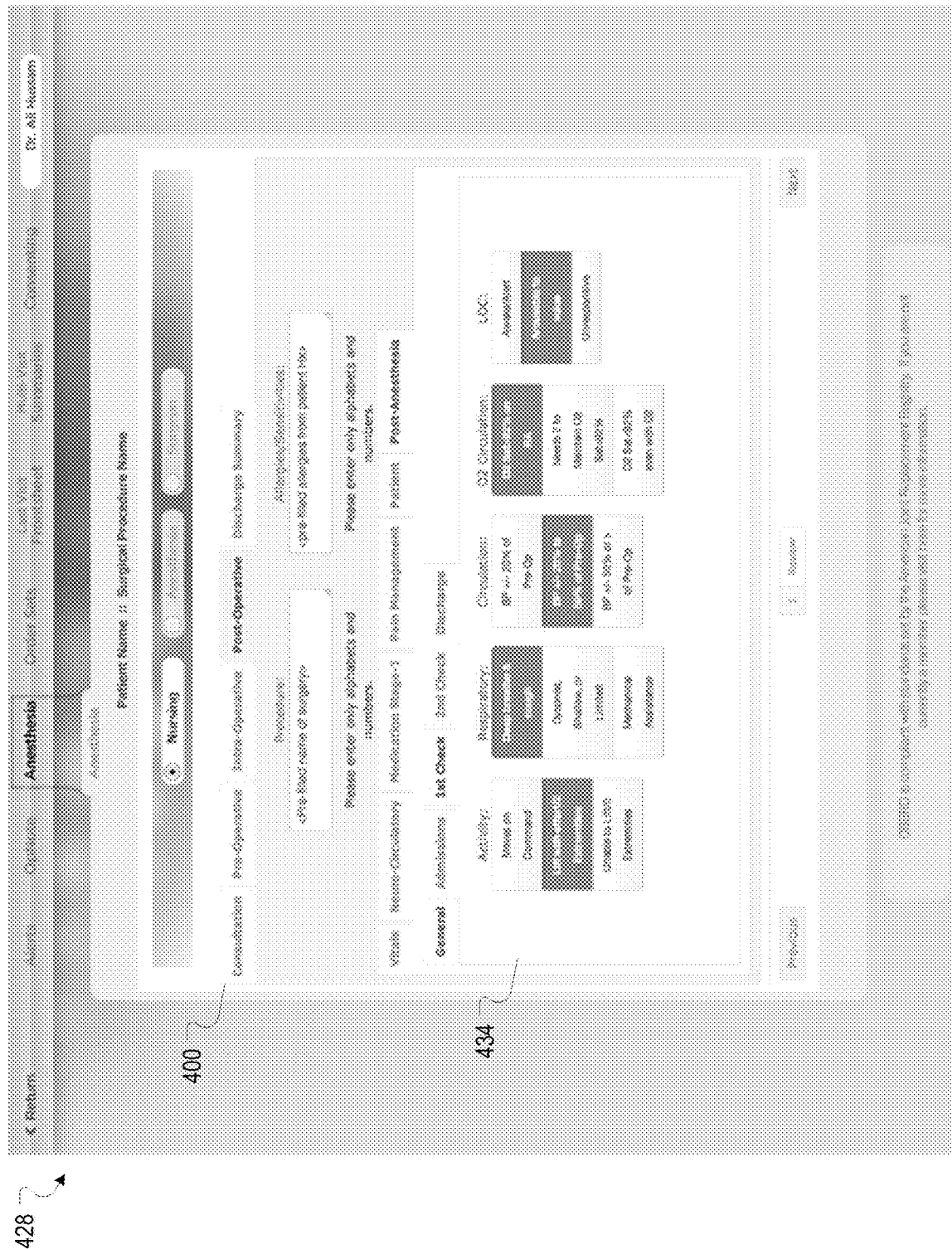
Figure 4H:
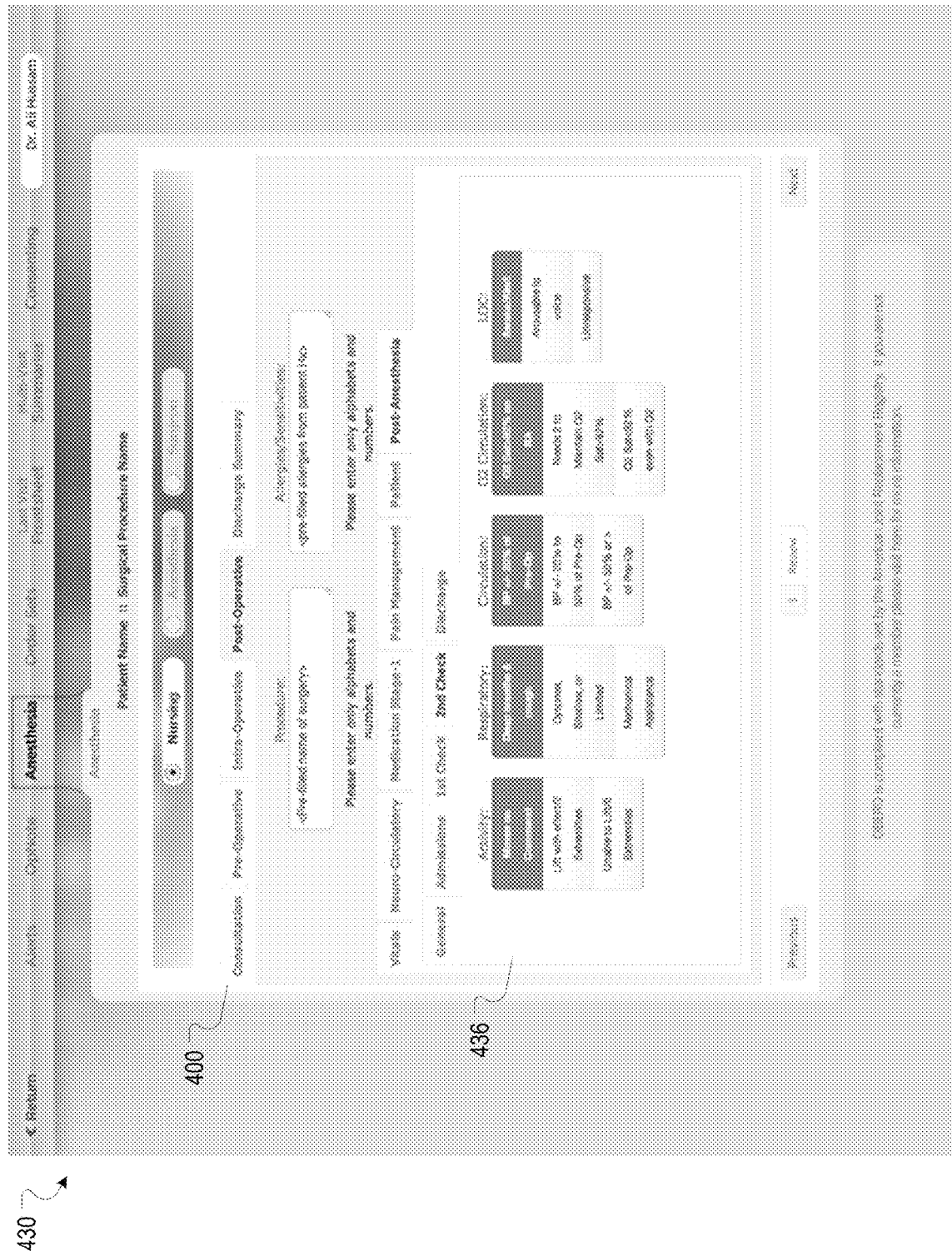
Figure 4I:
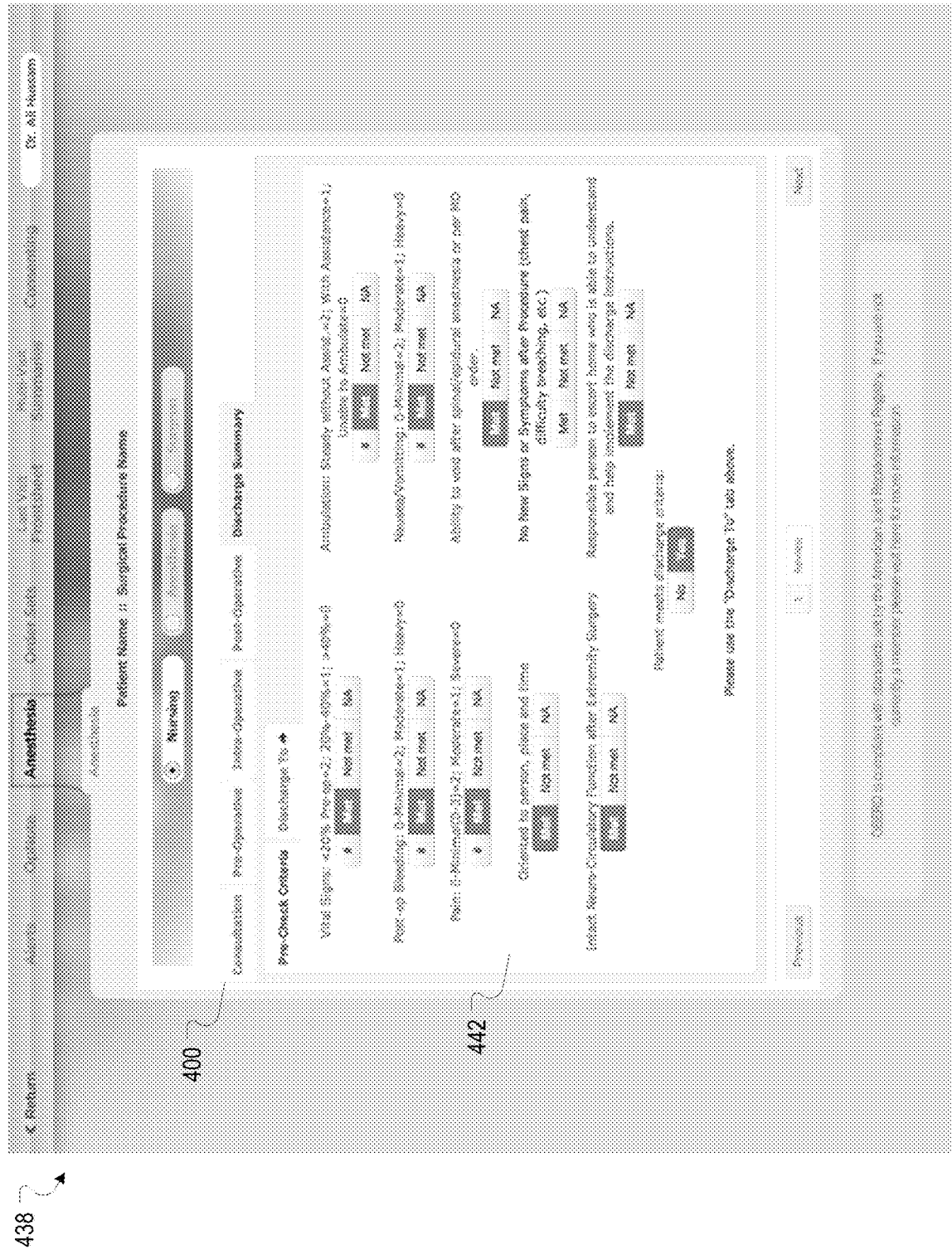
Figure 4J:
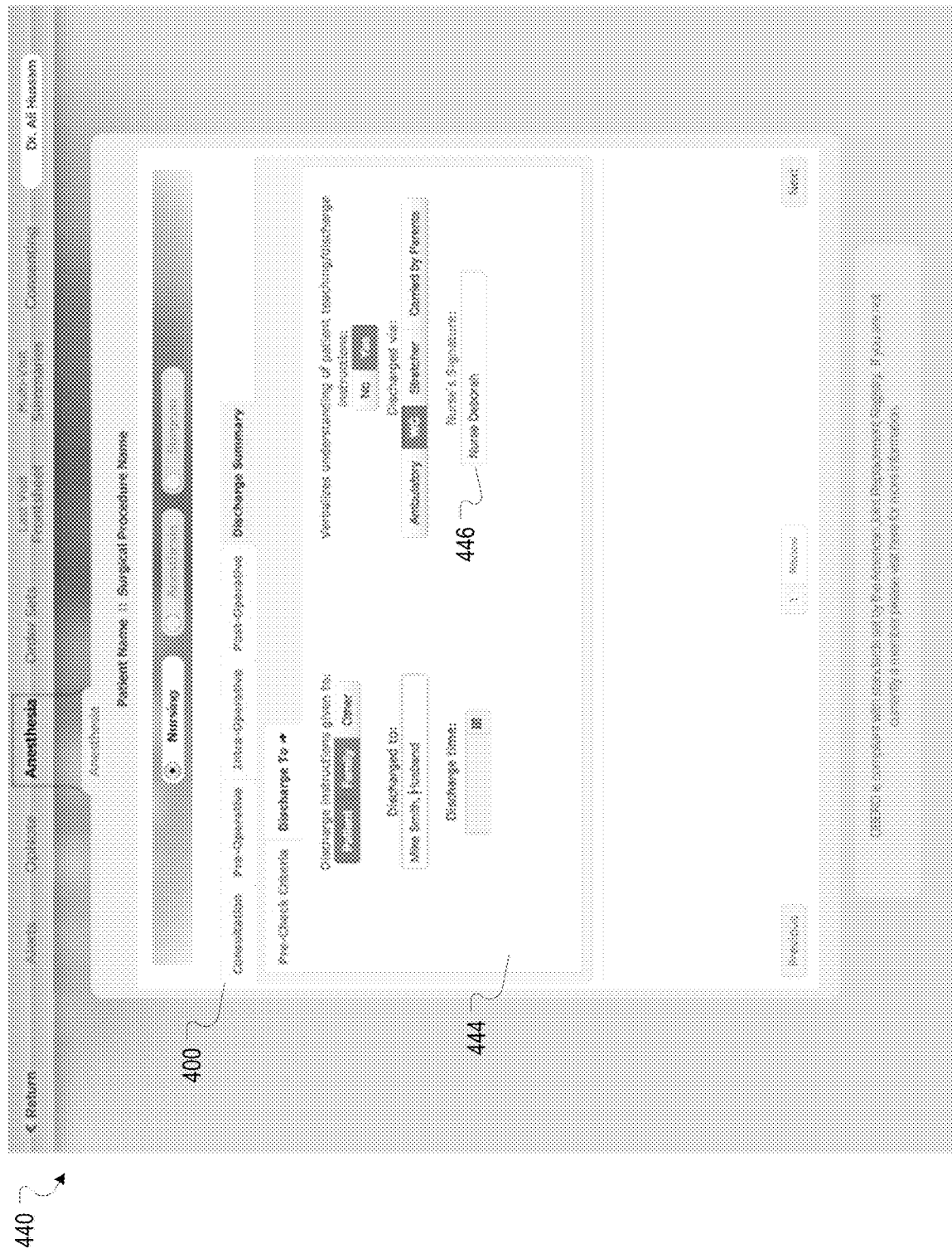

Referring to FIGS. 4A-4J, system 112 generates graphical user interfaces that present portions of a template pertaining to a surgical procedure performed on a patient. As shown in FIGS. 4A-4J, the portions include a group 400 of selectable tabs for switching among different portions of the template. The template includes a consultation portion (FIGS. 4A and 4B), a pre-operative portion (FIGS. 4C and 4D), an intra-operative portion (FIG. 4E), a post-operative portion (FIGS. 4F-4H), and a discharge portion (FIGS. 4I and 4J). The consultation portion and the pre-operative portion may be used for entry of data pertaining to a time period prior to the surgical procedure. The intra-operative portion may be used for entry of data pertaining to performance of the surgical procedure. The post-operative portion may be used for entry of data pertaining to an outcome of the surgical procedure or data related to recovery from the surgical procedure. The discharge portion may be used for entry of data pertaining to discharge of the patient from the surgical center.

FIG. 4A shows a graphical user interface 402 that presents the consultation portion 404 of the template. The consultation portion 404 includes groups of selectable fields, e.g., group 408, and data fields, e.g., data field 410. FIG. 4B shows the graphical user interface 402 after a user has entered medical data into some of the data fields, e.g., data field 412, and selected some of the selectable fields, e.g., selectable field 408, included in the template. FIGS. 4C and 4D show graphical user interfaces 414 and 416 that present a systems review portion 418 and an exam & anesthesia portion 420 of the pre-operative portion of the template. FIG. 4E shows a graphical user interface 422 that presents an anesthesia portion 424 of the intra-operative portion of the template. FIGS. 4F, 4G, and 4H show graphical user interfaces 426, 428, and 430 that present an admission portion 432, a first check portion 434, and a second check portion 436 of a post-anesthesia portion of the post-operative portion of the template. FIGS. 4I and 4J show graphical user interfaces 438 and 440 that present a pre-check criteria portion 442 and a discharge to portion 444 of the discharge portion of the template. The discharge to portion 444 may include a data field 446 for a user to electronically sign the operative note generated based on the medical data entered using the template.

The system 112 generates a surgical operative note from a populated template. The surgical operative note may include a summary of the surgical procedure. The operative note may include details of the surgical procedure. The surgical operative note may be structured according to the various portions included in the template from which the surgical operative note is generated. For example, the surgical operative note may be structured into various operative portions each relating to a stage of a surgical procedure. For a surgical operative note generated from the template described in FIGS. 4A-4J, for example, the surgical operative note may include a consultation portion, a pre-operative portion, an intra-operative portion, a post-operative portion, and a discharge portion.

Figure 5:
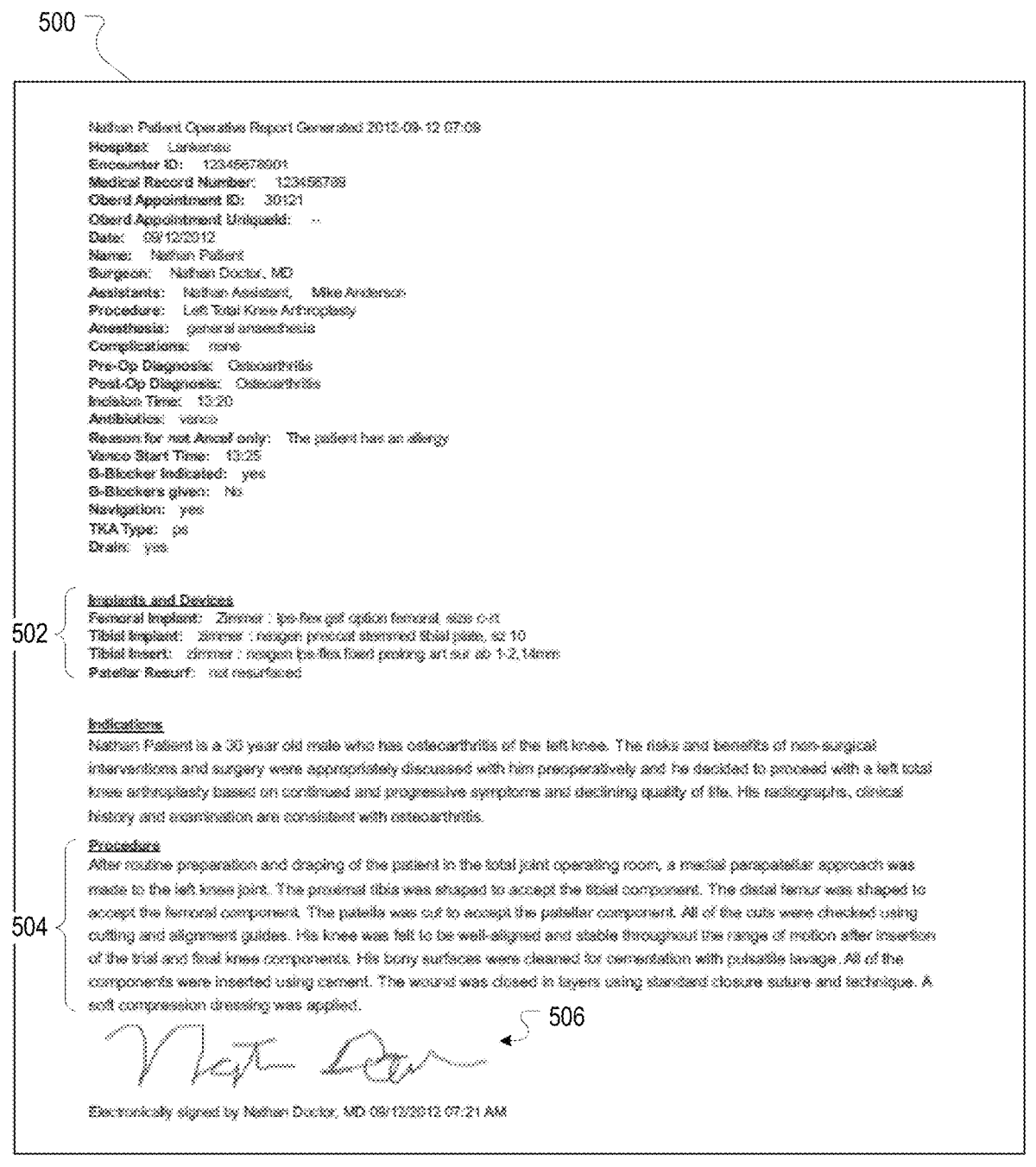

FIG. 5 shows an example of a surgical operative note 500 generated using a template. In the example of FIG. 5, the surgical operative note 500 includes information about the patient and the surgical procedure, including information pertaining to the implants and devices 502 implanted in the patient and details of the surgical procedure 504. The surgical operative note 500 includes an electronic signature 506 of the physician.

Figure 6:
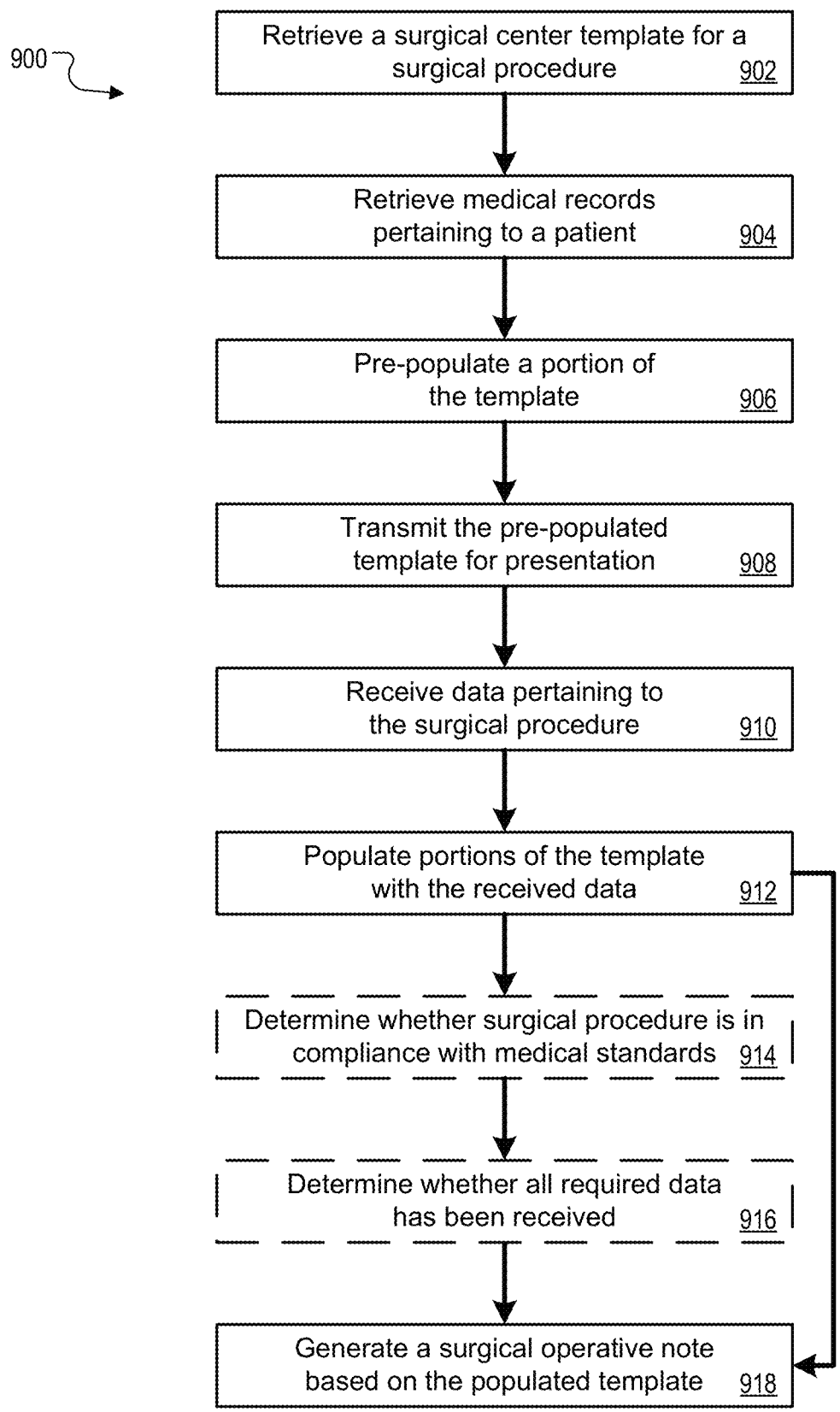
FIG. 6 is a flow chart of an example of a process for generating an operative note using a template.

FIG. 6 is a flow chart of an example of a process 600 for generating an operative note using a template. In operation, system 112 retrieves a surgical center template for a surgical procedure that is performed by a surgical center (902). The system 112 may retrieve the surgical center template in response to receiving a request from a device used by a physician to update medical data pertaining to a patient or to generate a surgical operative note for a surgical procedure. The surgical center template may include predefined data fields for entry of medical data. The surgical center template may include selectable fields for selection of an attribute of a patient on whom the surgical procedure is performed or an attribute of the surgical procedure. The surgical center template may include a visualization relating to the surgical procedure, such as a visualization of a portion of the body on which the surgical procedure is performed. The surgical center template may include various portions, such as a pre-operative portion, an intra-operative portion, a post-operative portion, and a discharge portion.

The system 112 retrieves medical records pertaining to the patient (904) and automatically pre-populates a portion of the template based on the contents of the retrieved medical records (906). The system 112 may pre-populate predefined data fields, pre-select selectable fields, pre-label a portion of the visualization, or a combination. The system 112 transmits, to the device used by the physician, the pre-populated template for presentation to the physician (908).

The system 112 receives, from the device used by the physician, data pertaining to the surgical procedure (910). The received data can include, for example, data entered into a predefined data field, data indicative of a selection of a selectable field of the template, data indicative of an annotation of a portion of a visualization, data indicative of a barcode associated with an implantable device that is used in the surgical procedure, or other suitable data.

The system 112 populates a portion of the template with the data received from the physician's device (912). If the received data is data indicative of a barcode associated with an implantable device, the system 112 may retrieve data associated with the barcode from a database, update a portion of the template with the retrieved data, and transmit the retrieved data to the physician's device for presentation to the physician.

The system 112 may determine whether the surgical procedure is in compliance with national medical standards or federal practices based on the data received from the physician's device (914). The system 112 may determine whether all required data pertaining to the surgical procedure has been received from the physician's device (916). For example, the system 112 may determine whether the physician has completed all portions of the template. If all required data has not been received, the system 112 may send a notification to the physician's device, to notify the physician that the required data has not been received.

The system 112 generates, based on the populated template, a surgical operative note for the surgical procedure (918). The surgical operative note can include, for example, a summary of the surgical procedure, details of the surgical procedure, information pertaining to an implant or a device used during the surgical procedure, or other information relating to the surgical procedure. To generate the operative note, the system 112 may structure the surgical operative note into various portions each relating to a stage of the surgical procedure. For example, the system 112 may structure the surgical operative note to include a consultation portion, a pre-operative portion, an intra-operative portion, a post-operative portion, and a discharge portion.

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be data in different formats such as text, graphics, images, sound, video, Hypertext Markup Language (HTML), as well as programs. Upon specification of a link by the user, the client computer makes a TCP/IP request to a Web server and receives data, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view data available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention.

What is claimed is:

1. A computer-implemented method comprising: receiving, by a data processing system with direct access to multiple distributed computers and from a device of a physician that does not have direct access to the multiple distributed computers, a request to generate a surgical operative note: retrieving, by the data processing system and from a first distributed computer, a surgical center template for a surgical procedure that is to be performed by a surgical center, wherein the surgical center template comprises one or more of (i) a plurality of predefined data fields for entry of medical data, and (ii) a plurality of selectable fields for selection of an attribute of a patient on whom the surgical procedure is performed or an attribute of the surgical procedure; retrieving, by the data processing system and from a second distributed computer that includes a data repository structuring information that represents one or more patient medical records, medical records pertaining to the patient; automatically pre-populating, by the data processing system, a portion of the surgical template retrieved from the first distributed computer based on contents of the medical data records that were retrieved from the second distributed computer, wherein automatically pre-populating the portion of the surgical template retrieved from the first distributed computer based on contents of the medical records retrieved from the second distributed computer comprises: generating, by the data processing system, visualization data that, when received and rendered by the device used by the physician, causes the device used by the physician to render a visualization related to a portion of an anatomy of the patient that is a subject of the surgical procedure, wherein generating the visualization related to the surgical procedure comprises: associating a label with one or more portions of the anatomy of the patient that pertains to an aspect of the surgical procedure to be performed; transmitting, by the data, processing system and to the device used by a physician, the pre-populated template for presentation to the physician, wherein the device used by the physician is located remotely from the data processing system and the multiple distributed computers; receiving, by the data processing system and from the device used by the physician, data pertaining to the surgical procedure input by the physician, wherein the received data pertaining to the surgical procedure input by the physician comprises at least one of (i) data entered into a predefined data field of the plurality of predefined data fields and (ii) data indicative of a selection of a selectable field in the plurality of selectable fields; storing, by the data processing system in a first data storage device, first data that specifies whether one or more conditions have been satisfied to initiate transmission of a notification to the device used by the physician requesting completion of the template; executing, by the data processing system, computer code that correlates data that includes the first data, the template, and the received data pertaining to the surgical procedure; determining, by the data processing system and based on the correlated data, whether each of a plurality of portions of the template have been completed; in response to determining, by the data processing system, that the physician has failed to complete a portion of the plurality of portions of the template, executing, by the data processing system, computer code that initiates transmission of the notification to the device used by the physician requesting completion of the template; and upon determining, by the data processing system, that the physician has completed all portions of the template, generating, by the data processing system and based on the populated template from the first distributed computer that includes fields structuring (i) data retrieved from the second distributed computer and (ii) data pertaining to the surgical procedure that was input by the physician using the device located remotely from the computer that stores the database, a surgical operative note for the surgical procedure, with the surgical operative note comprising a summary of the surgical procedure.

2. The computer-implemented method of claim 1, wherein the surgical operative note comprises one or more details of an implant or a device used during the surgical procedure.

3. The computer-implemented method of claim 1, wherein generating the surgical operative note comprises:
structuring the surgical operative note into a plurality of operative portions, each of the plurality of operative portions related to a stage of a plurality of stages of the surgical procedure.

4. The computer-implemented method of claim 3, wherein the plurality of operative portions comprise a consultation portion, a pre-operative portion, an intra-operative portion, a post-operative portion, and a discharge portion.

5. The computer-implemented method of claim 1, wherein the surgical center template comprises:
pre-operative portion for entry of data pertaining to a time period prior to the surgical procedure;
an intra-operative portion for entry of data pertaining to performance of the surgical procedure;
a post-operative portion for entry of data pertaining to an outcome of the surgical procedure or data related to recovery from the surgical procedure; and
a discharge portion for entry of data pertaining to discharge from the surgical center.

6. The computer-implemented method of claim 1, wherein receiving, from the device used by the physician, data pertaining to the surgical procedure comprises:
receiving data indicative of an annotation of a portion of the visualization.

7. The computer-implemented method of claim 1, wherein receiving, from the device used by the physician, data pertaining to the surgical procedure comprises:
receiving data indicative of a barcode associated with an implantable device that is used in the surgical procedure; and
the method further comprises:
retrieving data associated with the barcode from a data repository;
updating a portion of the surgical center template with the retrieved data that is associated with the bar code; and
transmitting, to the device used by the physician, the retrieved data for presentation with the surgical center template.

8. The computer-implemented method of claim 1, further comprising:
determining, based on the received data pertaining to the surgical procedure, whether the surgical procedure is in compliance with national medical standards.

9. One or more machine-readable hardware storage devices storing instructions that are executable by one or more processing devices of a data processing system to perform operations comprising: receiving, by the data processing system with direct access to multiple distributed computers and from a device of a physician that does not have direct access to the multiple distributed computers, a request to generate a surgical operative note; retrieving, by the data processing system and from a first distributed computer, a surgical center template for a surgical procedure that is to be performed by a surgical center, wherein the surgical center template comprises one or more of (i) a plurality of predefined data fields for entry of medical data, and (ii) a plurality of selectable fields for selection of an attribute of a patient on whom the surgical procedure is performed or an attribute of the surgical procedure; retrieving, by the data processing system and from a second distributed computer that includes a data repository structuring information that represents one or more patient medical records, medical records pertaining to the patient; automatically pre-populating, by the data processing system, a portion of the surgical template retrieved from the first distributed computer based on contents of the medical data records that were retrieved from the second distributed computer, wherein automatically pre-populating the portion of the surgical template retrieved from the first distributed computer based on contents of the medical records retrieved from the second distributed computer comprises: generating, by the data processing system, visualization data that, when received and rendered by the device used by the physician, causes the device used by the physician to render a visualization related to a portion of an anatomy of the patient that is a subject of the surgical procedure, wherein generating the visualization related to the surgical procedure comprises; associating a label with one or more portions of the anatomy of the patient that pertains to an aspect of the surgical procedure to be performed; transmitting, by the data processing system and to the device used by a physician, the pre-populated template for presentation to the physician, wherein the device used by the physician is located remotely from the data processing system and the multiple distributed computers; receiving, by the data processing system and from the device used by the physician, data pertaining to the surgical procedure input by the physician, wherein the received data pertaining to the surgical procedure input by the physician comprises at least one of (i) data entered into a predefined data field of the plurality of predefined data fields and (ii) data indicative of a selection of a selectable field in the plurality of selectable fields; storing, by the data processing system in a first data storage device, first data that specifies whether one or more conditions have been satisfied to initiate transmission of a notification to the device used by the physician requesting completion of the template; executing, by the data processing system, computer code that correlates data that includes the first data, the template, and the received data pertaining to the surgical procedure; determining, by the data processing system and based on the correlated data, whether each of a plurality of portions of the template have been completed; in response to determining, by the data processing system, that the physician has failed to complete a portion of the plurality of portions of the template, executing, by the data processing system, computer code that initiates transmission of the notification to the device used by the physician requesting completion of the template; and upon determining, by the data processing system, that the physician has completed at portions of the template, generating, by the data processing system and based on the populated template from the first distributed computer that includes fields structuring (i) data retrieved from the second distributed computer and (ii) data pertaining to the surgical procedure that was input by the physician using the device located remotely from the computer that stores the database, a surgical operative note for the surgical procedure, with the surgical operative note comprising a summary of the surgical procedure.

10. The one or more machine-readable hardware storage devices of claim 9, wherein the surgical operative note comprises one or more details of an implant or a device used during the surgical procedure.

11. The one or more machine-readable hardware storage devices of claim 9, wherein generating the surgical operative note comprises:

structuring the surgical operative note into a plurality of operative portions, each of the plurality of operative portions related to a stage of a plurality of stages of the surgical procedure.

12. The one or more machine-readable hardware storage devices of claim 11, wherein the plurality of operative portions comprise a consultation portion, a pre-operative portion, an intra-operative portion, a post-operative portion, and a discharge portion.

13. The one or more machine-readable hardware storage devices of claim 9, wherein the surgical center template comprises:

pre-operative portion for entry of data pertaining to a time period prior to the surgical procedure;

an intra-operative portion for entry of data pertaining to performance of the surgical procedure;

a post-operative portion for entry of data pertaining to an outcome of the surgical procedure or data related to recovery from the surgical procedure; and a discharge portion for entry of data pertaining to discharge from the surgical center.

14. An electronic system comprising: one or more process devices; and one or more machine-readable hardware storage devices storing instructions that are executable by one or more processing devices to perform operations comprising: receiving, by electronic system with direct access to multiple distributed computers and from a device of a physician that does not have direct access to the multiple distributed computers, a request to generate a surgical operative note; retrieving, by the electronic system and from a first distributed computer, a surgical center template for a surgical procedure that is to be performed by a surgical center, wherein the surgical center template comprises one or more of (i) a plurality of predefined data fields for entry of medical data, and (ii) a plurality of selectable fields for selection of an attribute of a patient on whom the surgical procedure is performed or an attribute of the surgical procedure; retrieving, by the electronic system and from a second distributed computer that includes a data repository structuring information that represents one or more patient medical records, medical records pertaining to the patient; automatically pre-populating, by the electronic system, a portion of the surgical template retrieved from the first distributed computer based on contents of the medical data records that were retrieved from the second distributed computer, wherein automatically pre-populating the portion of the surgical template retrieved from the first distributed computer based on contents of the medical records retrieved from the second distributed computer comprises: generating, by the electronic system, visualization data that, when received and rendered by the device used by the physician, causes the device used by the physician to render a visualization related to a portion of an anatomy of the patient that is a subject of the surgical procedure, wherein generating the visualization related to the surgical procedure comprises: associating a label with one or more portions of the anatomy of the patient that pertains to an aspect of the surgical procedure to be performed; transmitting, by the electronic system and to the device used by a physician, the pre-populated template for presentation to the physician, wherein the device used by the physician is located remotely from the electronic system and the multiple distributed computers; receiving, by the electronic system and from the device used by the physician, data pertaining to the surgical procedure input by the physician, wherein the received data pertaining to the surgical procedure input by the physician comprises at least one of Qi data entered into a predefined data field of the plurality of predefined data fields and (ii) data indicative of a selection of a selectable field in the plurality of selectable fields; storing, by the electronic system in a first data storage device, first data that specifies whether one or more conditions have been satisfied to initiate transmission of a notification to the device used by the physician requesting completion of the template; executing, by the electronic system, computer code that correlates data that includes the first data, the template, and the received data pertaining to the surgical procedure; determining, by the electronic system and based on the correlated data, whether each of a plurality of portions of the template have been completed; in response to determining, by the electronic system, that the physician has failed to complete a portion of the plurality of portions of the template, executing, by the electronic system, computer code that initiates transmission of the notification to the device used by the physician requesting completion of the template; and upon determining, by the electronic system, that the physician has completed all portions of the template, generating, by the electronic system and based on the populated template from the first distributed computer that includes fields structuring (i) data retrieved from the second distributed computer and (ii) data pertaining to the surgical procedure that was input by the physician using the device located remotely from the computer that stores the database, a surgical operative note for the surgical procedure, with the surgical operative note comprising a summary of the surgical procedure.

15. The electronic system of claim 14, wherein the surgical operative note comprises one or more details of an implant or a device used during the surgical procedure.

16. The electronic system of claim 14, wherein generating the surgical operative note comprises:

structuring the surgical operative note into a plurality of operative portions, each of the plurality of operative portions related to a stage of a plurality of stages of the surgical procedure.

17. The electronic system of claim 16, wherein the plurality of operative portions comprise a consultation portion, a pre-operative portion, an intra-operative portion, a post-operative portion, and a discharge portion.

* * * * *